(12) United States Patent
Ashraf et al.

(10) Patent No.: US 11,999,150 B2
(45) Date of Patent: Jun. 4, 2024

(54) NONWOVEN WEBS WITH ONE OR MORE REPEAT UNITS

(71) Applicant: The Procter & Gamble Company, Cincinnati, OH (US)

(72) Inventors: Arman Ashraf, Mason, OH (US); Sara L. Giovanni, Cincinnati, OH (US); Keith Alvarado, Cincinnati, OH (US); Brittany D. Canfield, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1046 days.

(21) Appl. No.: 16/861,258

(22) Filed: Apr. 29, 2020

(65) Prior Publication Data

US 2020/0345563 A1    Nov. 5, 2020

Related U.S. Application Data

(60) Provisional application No. 62/842,807, filed on May 3, 2019, provisional application No. 62/842,792, filed on May 3, 2019.

(51) Int. Cl.
*A61F 13/49* (2006.01)
*A61F 13/15* (2006.01)
(Continued)

(52) U.S. Cl.
CPC ........ *B32B 5/022* (2013.01); *A61F 13/15203* (2013.01); *A61F 13/51108* (2013.01);
(Continued)

(58) Field of Classification Search
None
See application file for complete search history.

(56) References Cited

U.S. PATENT DOCUMENTS 4,005,169 A * 1/1977 Cumbers ................ D04H 1/541
264/293
D244,319 S * 5/1977 Kies ................................ D5/53
(Continued)

FOREIGN PATENT DOCUMENTS

CN         1685099        10/2005
CN      101864640 A   * 10/2010
(Continued)

OTHER PUBLICATIONS

Machine Translation of EP-882828-A1, Dec. 1998 (Year: 1998).*
(Continued)

*Primary Examiner* — Jeffrey A Vonch
(74) *Attorney, Agent, or Firm* — Christian M. Best

(57) ABSTRACT

A nonwoven web for an absorbent article is provided. The nonwoven web includes a first surface and a second surface. The nonwoven web includes a repeat unit comprising a visually discernible pattern of three-dimensional features on the first surface or the second surface. The three-dimensional features comprise one or more first regions and a plurality of second regions. The one or more first regions are different than the plurality of second regions. The one or more first regions comprise a plurality of substantially linear segments. A first group of the plurality of substantially linear segments intersects with a second group of the plurality of substantially linear segments at angles of intersection. The angles of intersection are in the range of about 70 degrees to about 110 degrees.

20 Claims, 28 Drawing Sheets

(51) Int. Cl.

| | | |
|---|---|---|
| *A61F 13/511* | (2006.01) | |
| *A61F 13/514* | (2006.01) | |
| *B32B 3/30* | (2006.01) | |
| *B32B 5/02* | (2006.01) | |
| *D04H 1/4291* | (2012.01) | |
| *A61F 13/42* | (2006.01) | |
| *A61F 13/534* | (2006.01) | |
| *B32B 5/16* | (2006.01) | |
| *B32B 5/30* | (2006.01) | |
| *D04H 1/495* | (2012.01) | |

(52) U.S. Cl.
CPC .......... *A61F 13/51121* (2013.01); *B32B 3/30* (2013.01); *D04H 1/4291* (2013.01); *A61F 2013/15243* (2013.01); *A61F 2013/15373* (2013.01); *A61F 2013/15406* (2013.01); *A61F 2013/15422* (2013.01); *A61F 13/42* (2013.01); *A61F 13/534* (2013.01); *B32B 5/16* (2013.01); *B32B 5/30* (2013.01); *B32B 2250/03* (2013.01); *B32B 2250/40* (2013.01); *B32B 2262/0253* (2013.01); *B32B 2264/0214* (2013.01); *B32B 2307/726* (2013.01); *B32B 2555/02* (2013.01); *D04H 1/495* (2013.01)

(56) References Cited

U.S. PATENT DOCUMENTS

| | | | |
|---|---|---|---|
| 4,088,726 A * | 5/1978 | Cunbers | D04H 1/549 264/293 |
| 4,333,979 A | 6/1982 | Sciaraffa et al. | |
| 4,493,868 A * | 1/1985 | Meitner | B32B 5/26 156/290 |
| 4,741,941 A | 5/1988 | Englebert et al. | |
| 4,970,104 A | 11/1990 | Radwanski | |
| 5,334,289 A | 8/1994 | Trokhan et al. | |
| 5,514,523 A * | 5/1996 | Trokhan | B29C 39/148 162/902 |
| 5,575,874 A | 11/1996 | Griesbach et al. | |
| 5,595,567 A * | 1/1997 | King | A44B 18/0011 D8/382 |
| 5,599,420 A | 2/1997 | Yeo et al. | |
| 5,643,653 A | 7/1997 | Griesbach, III et al. | |
| D381,811 S * | 8/1997 | du Grosriez | D5/53 |
| D383,003 S * | 9/1997 | Hepford | D5/53 |
| 5,725,927 A | 3/1998 | Zilg et al. | |
| D402,475 S * | 12/1998 | Mattheeussen | D5/35 |
| 5,858,504 A | 1/1999 | Steven | |
| 5,895,623 A | 4/1999 | Trokhan et al. | |
| 5,916,661 A | 6/1999 | Benson et al. | |
| 6,139,941 A | 10/2000 | Jankevics et al. | |
| 6,149,768 A * | 11/2000 | Hepford | D21F 11/14 162/134 |
| 6,319,455 B1 | 11/2001 | Kauschke et al. | |
| 6,331,268 B1 | 12/2001 | Kauschke et al. | |
| 6,331,345 B1 | 12/2001 | Kauschke et al. | |
| 6,361,638 B2 | 3/2002 | Takai et al. | |
| 6,383,431 B1 | 5/2002 | Dobrin et al. | |
| 6,395,957 B1 | 5/2002 | Chen et al. | |
| 6,436,512 B1 | 8/2002 | Kauschke et al. | |
| D465,093 S * | 11/2002 | Jahner | D5/25 |
| D472,056 S * | 3/2003 | Jahner | D5/25 |
| 6,576,091 B1 * | 6/2003 | Cabell | G03F 7/12 428/196 |
| 6,610,390 B1 | 8/2003 | Kauschke | B32B 25/10 442/325 |
| 6,632,504 B1 | 10/2003 | Gillespie et al. | |
| 6,673,418 B1 | 1/2004 | DeOlivera et al. | |
| 6,818,802 B2 | 11/2004 | Takai et al. | |
| D505,552 S * | 5/2005 | Pommier | D5/53 |
| D541,053 S * | 4/2007 | Sanders | D5/58 |
| 7,507,463 B2 | 3/2009 | Noda et al. | |
| 7,553,535 B2 | 6/2009 | Noda et al. | |
| 7,662,462 B2 | 2/2010 | Noda et al. | |
| 7,897,240 B2 | 3/2011 | Noda et al. | |
| 7,954,213 B2 | 6/2011 | Mizutani et al. | |
| 7,955,549 B2 | 6/2011 | Noda et al. | |
| 8,143,177 B2 | 3/2012 | Noda et al. | |
| 8,183,431 B2 | 5/2012 | Noda et al. | |
| 8,273,941 B2 | 9/2012 | Uematsu et al. | |
| 8,304,600 B2 | 11/2012 | Noda et al. | |
| 8,574,209 B2 | 11/2013 | Nishitani et al. | |
| 8,585,666 B2 | 11/2013 | Weisman et al. | |
| 8,758,569 B2 | 6/2014 | Aberg et al. | |
| 8,853,108 B2 | 10/2014 | Ahoniemi et al. | |
| 8,865,965 B2 | 10/2014 | Sato et al. | |
| 8,906,275 B2 | 12/2014 | Davis et al. | |
| D720,544 S * | 1/2015 | Seitzinger | D5/57 |
| 9,095,477 B2 | 8/2015 | Yamaguchi et al. | |
| 9,156,229 B2 | 10/2015 | Yoda et al. | |
| 9,205,005 B2 | 12/2015 | Kikuchi et al. | |
| 9,453,303 B2 | 9/2016 | Aberg et al. | |
| D772,583 S * | 11/2016 | Hannen | B32B 21/042 D5/57 |
| 9,732,454 B2 | 8/2017 | Davis et al. | |
| 9,877,876 B2 | 1/2018 | Huang et al. | |
| 9,903,070 B2 | 2/2018 | Mourad et al. | |
| 9,968,496 B2 | 5/2018 | Barbosa et al. | |
| 10,190,244 B2 | 1/2019 | Ashraf et al. | |
| D897,118 S * | 9/2020 | Dewar | D5/55 |
| 2001/0029141 A1 | 10/2001 | Mizutani et al. | |
| 2002/0049419 A1 * | 4/2002 | Mizutani | A61F 13/15699 604/385.01 |
| 2002/0052584 A1 * | 5/2002 | Forgar | A61F 13/4902 604/358 |
| 2002/0068150 A1 * | 6/2002 | Taneichi | D04H 1/559 428/137 |
| 2002/0153271 A1 | 10/2002 | McManus et al. | |
| 2002/0193032 A1 | 12/2002 | Newkirk et al. | |
| 2003/0093044 A1 * | 5/2003 | Wahlstrom | A61F 13/512 604/378 |
| 2003/0093045 A1 | 5/2003 | Jensen | |
| 2003/0119404 A1 | 6/2003 | Belau et al. | |
| 2003/0125687 A1 | 7/2003 | Gubernick et al. | |
| 2003/0203162 A1 | 10/2003 | Christopher et al. | |
| 2003/0203691 A1 | 10/2003 | Fenwick et al. | |
| 2003/0211802 A1 | 11/2003 | Keck et al. | |
| 2003/0215602 A1 * | 11/2003 | Andersson | B32B 37/1292 428/116 |
| 2004/0029479 A1 * | 2/2004 | Snider | D04H 1/495 28/104 |
| 2004/0059309 A1 | 3/2004 | Nortman | |
| 2005/0148971 A1 | 7/2005 | Kuroda et al. | |
| 2005/0175269 A1 | 8/2005 | Ashton et al. | |
| 2005/0175296 A1 | 8/2005 | Massey | |
| 2006/0087053 A1 | 4/2006 | O'Donnell et al. | |
| 2006/0105075 A1 | 5/2006 | Otsubo | |
| 2006/0189954 A1 | 8/2006 | Kudo et al. | |
| 2007/0026753 A1 | 2/2007 | Neely et al. | |
| 2007/0045143 A1 | 3/2007 | Clough et al. | |
| 2007/0045144 A1 | 3/2007 | Wheeler et al. | |
| 2007/0049153 A1 | 3/2007 | Dunbar et al. | |
| 2007/0179466 A1 | 8/2007 | Tremblay et al. | |
| 2007/0298214 A1 | 12/2007 | Noda et al. | |
| 2007/0298667 A1 | 12/2007 | Noda et al. | |
| 2008/0149292 A1 | 6/2008 | Scherb | |
| 2008/0281287 A1 * | 11/2008 | Marcelo | A61F 13/4756 604/383 |
| 2009/0240222 A1 | 9/2009 | Tomoko et al. | |
| 2010/0036346 A1 | 2/2010 | Hammons | |
| 2010/0048072 A1 | 2/2010 | Kauschke | |
| 2010/0178456 A1 * | 7/2010 | Kuroda | B32B 3/266 428/136 |
| 2011/0118689 A1 * | 5/2011 | Een | A61F 13/15593 604/385.24 |
| 2011/0250378 A1 | 10/2011 | Eaton et al. | |
| 2012/0004633 A1 | 1/2012 | Marcelo et al. | |
| 2012/0165774 A1 * | 6/2012 | Otsubo | A61F 13/51476 604/366 |
| 2012/0196091 A1 | 8/2012 | Mizutani et al. | |

(56) References Cited

U.S. PATENT DOCUMENTS

| | | | |
|---|---|---|---|
| 2012/0245550 A1* | 9/2012 | Sakaguchi | A61F 13/627 604/391 |
| 2012/0315440 A1* | 12/2012 | Ichikawa | D04H 1/54 428/156 |
| 2013/0112584 A1 | 5/2013 | Gaspari et al. | |
| 2013/0139960 A1 | 6/2013 | Maruyama et al. | |
| 2013/0167305 A1* | 7/2013 | Weisman | C11D 17/047 510/439 |
| 2013/0171421 A1* | 7/2013 | Weisman | D01F 1/10 264/103 |
| 2013/0236700 A1 | 9/2013 | Yamanaka et al. | |
| 2013/0237942 A1* | 9/2013 | Beckert | A61F 13/622 604/389 |
| 2013/0253461 A1* | 9/2013 | Xu | A61F 13/51121 428/156 |
| 2013/0280481 A1* | 10/2013 | Mitsuno | A61F 13/51104 428/196 |
| 2013/0320584 A1 | 12/2013 | Davis et al. | |
| 2014/0037906 A1* | 2/2014 | Polosa | D04H 1/54 428/167 |
| 2014/0127460 A1 | 5/2014 | Xu et al. | |
| 2014/0234575 A1 | 8/2014 | Mitsuno et al. | |
| 2014/0276508 A1* | 9/2014 | Wright | A61F 13/539 604/365 |
| 2014/0276517 A1 | 9/2014 | Chester et al. | |
| 2014/0296815 A1 | 10/2014 | Takken et al. | |
| 2014/0305570 A1 | 10/2014 | Matsunaga et al. | |
| 2014/0324009 A1 | 10/2014 | Lee et al. | |
| 2015/0057627 A1* | 2/2015 | Noda | A61F 13/5126 604/378 |
| 2015/0107063 A1* | 4/2015 | Baldauf | B32B 5/26 24/449 |
| 2015/0140240 A1* | 5/2015 | Pleyber | D04H 1/00 428/141 |
| 2015/0173967 A1 | 6/2015 | Kreuzer et al. | |
| 2015/0250663 A1* | 9/2015 | Wagner | A61F 13/512 604/378 |
| 2015/0265473 A1 | 9/2015 | Hammons et al. | |
| 2015/0282999 A1 | 10/2015 | Arizti et al. | |
| 2016/0067119 A1 | 3/2016 | Weisman et al. | |
| 2016/0106633 A1 | 4/2016 | Nagata et al. | |
| 2016/0129661 A1 | 5/2016 | Arora et al. | |
| 2016/0136009 A1 | 5/2016 | Weisman et al. | |
| 2017/0014281 A1 | 1/2017 | Xie et al. | |
| 2017/0022660 A1* | 1/2017 | Suer | D21H 27/02 |
| 2017/0027774 A1 | 2/2017 | Ashraf et al. | |
| 2017/0029993 A1 | 2/2017 | Ashraf et al. | |
| 2017/0029994 A1* | 2/2017 | Ashraf | A61F 13/51104 |
| 2017/0056256 A1 | 3/2017 | Smith et al. | |
| 2017/0121873 A1 | 5/2017 | Kimura et al. | |
| 2017/0191198 A1 | 7/2017 | Ashraf et al. | |
| 2017/0258650 A1 | 9/2017 | Rosati et al. | |
| 2017/0319399 A1* | 11/2017 | Desai | B32B 21/042 |
| 2017/0348163 A1 | 12/2017 | Lakso et al. | |
| 2018/0168893 A1 | 6/2018 | Ashraf et al. | |
| 2018/0214318 A1 | 8/2018 | Ashraf et al. | |
| 2018/0214321 A1 | 8/2018 | Ashraf et al. | |
| 2018/0216269 A1 | 8/2018 | Ashraf et al. | |
| 2018/0216270 A1 | 8/2018 | Ashraf et al. | |
| 2018/0216271 A1 | 8/2018 | Ashraf et al. | |
| 2019/0003079 A1 | 1/2019 | Ashraf et al. | |
| 2019/0003080 A1 | 1/2019 | Ashraf et al. | |
| 2019/0060135 A1 | 2/2019 | Kawka | |
| 2019/0112737 A1 | 4/2019 | Ashraf et al. | |
| 2019/0161897 A1* | 5/2019 | Mecl | D04H 3/14 |
| 2020/0054501 A1 | 2/2020 | Seto et al. | |
| 2020/0347533 A1 | 11/2020 | Ashraf et al. | |
| 2021/0189619 A1* | 6/2021 | Weis | D04H 1/5418 |

FOREIGN PATENT DOCUMENTS

| | | | |
|---|---|---|---|
| CN | 101914838 A | * 12/2010 | |
| DE | 102004053805 B3 | * 8/2006 | A44B 18/0011 |
| EP | 882828 A1 | * 12/1998 | A44B 18/0011 |
| EP | 2660377 | 4/2014 | |
| EP | 2926787 A1 | 10/2015 | |
| JP | 57167442 A | * 10/1982 | D04H 1/54 |
| JP | 09195154 A | * 7/1997 | |
| JP | 11335960 A | * 12/1999 | A44B 18/0011 |
| JP | 2005245483 A | * 9/2005 | D04H 1/54 |
| JP | 2006281545 A | * 10/2006 | |
| JP | 2011-015707 | 1/2011 | |
| JP | 2011137262 A | * 7/2011 | |
| JP | 2012149371 A | * 8/2012 | D04H 1/54 |
| JP | 2012239531 A | * 12/2012 | |
| JP | 2014-097257 | 5/2014 | |
| JP | 2014-188042 | 10/2014 | |
| JP | 2015043895 A | * 3/2015 | |
| JP | 2015112306 A | * 6/2015 | A44B 18/0011 |
| JP | 2015112339 A | * 6/2015 | |
| JP | 2015112340 A | * 6/2015 | |
| JP | 2016116582 A | * 6/2016 | A61F 13/512 |
| JP | 2017104197 A | * 6/2017 | A61F 13/15 |
| JP | 2017196064 A | * 11/2017 | A61F 13/15 |
| WO | WO-0180680 A1 | * 11/2001 | A44B 18/0011 |
| WO | 2009021473 A1 | 2/2009 | |
| WO | 2011024489 A1 | 3/2011 | |
| WO | 2012006300 A1 | 1/2012 | |
| WO | WO201286730 | 6/2012 | |
| WO | WO-2012086766 A1 | * 6/2012 | D04H 1/54 |
| WO | WO-2012169576 A1 | * 12/2012 | A61F 13/539 |
| WO | WO 2003-015681 | 2/2013 | |
| WO | WO201318846 | 2/2013 | |
| WO | WO 2013-084977 | 6/2013 | |
| WO | WO201399625 | 7/2013 | |
| WO | WO2013145966 | 10/2013 | |
| WO | WO-2013146701 A1 | * 10/2013 | A61F 13/51108 |
| WO | WO-2014024643 A1 | * 2/2014 | A61F 13/15699 |
| WO | 2014047160 A1 | 3/2014 | |
| WO | 2014115401 A1 | 7/2014 | |
| WO | WO-2016098848 A1 | * 6/2016 | A61F 13/49 |
| WO | WO-2016204131 A1 | * 12/2016 | A44B 18/00 |
| WO | WO-2017038030 A1 | * 3/2017 | A61F 13/511 |
| WO | WO-2017086327 A1 | * 5/2017 | A61F 13/511 |
| WO | WO 2017-105997 | 6/2017 | |
| WO | WO2017110695 | 6/2017 | |
| WO | WO-2017131597 A1 | * 8/2017 | |
| WO | WO-2018030181 A1 | * 2/2018 | A61F 13/511 |

OTHER PUBLICATIONS

Machine Translation of JP-11335960-A, Dec. 1999 (Year: 1999).*
Machine Translation of JP-2015112306-A, Jun. 2015 (Year: 2015).*
Machine Translation of JP-2015112339-A, Jun. 2015 (Year: 2015).*
Lorasutyagina, Illustration: Black And White Abstract Backdrop. Plaid Fabric Texture. Random Lines. Seamless Pattern., Jul. 2017, Megapixl <https://www.megapixl.com/black-and-white-abstract-backdrop-plaid-fabric-texture-random-lines-seamless-pattern-illustration-55242267> (Year: 2017).*
International Search Report and Written Opinion; Application Ser. No. PCT /US2020/030334; dated Aug. 28, 2020, 9 pages.
All Office Actions, U.S. Appl. No. 16/861,261.

* cited by examiner

NONWOVEN WEBS WITH ONE OR MORE REPEAT UNITS

CROSS REFERENCE TO RELATED APPLICATION

This application claims priority, under 35 U.S.C. § 119(e), to of U.S. Provisional Patent Application Ser. Nos. 62/842,792 and 62/842,807, both filed on May 3, 2019, the entire disclosures of both of which are hereby incorporated by reference herein.

FIELD

The present disclosure is directed to nonwoven webs with one or more repeat units. The present disclosure is also directed to absorbent articles comprising one or more nonwoven webs with one or more repeat units.

BACKGROUND

Nonwoven webs are used in many industries, including the medical, hygiene, and cleaning industries. Absorbent articles comprising nonwoven webs are used in the hygiene industry to contain and absorb bodily exudates (i.e., urine, bowel movements, and menses) in infants, children, and adults. Absorbent articles may include, but not be limited to, diapers, pants, adult incontinence products, feminine care products, and absorbent pads. Various components of these absorbent articles comprise nonwoven webs. Some example components that comprise nonwoven webs are outer cover nonwoven materials, topsheets, waistbands, leg cuffs, waist cuffs, ears, belts, and acquisition materials, for example. Consumers desire high quality nonwoven webs that function well for their intended purpose. Texture is one aspect of nonwoven webs that consumer find beneficial. As such, some nonwoven webs comprise texture patterns.

Visually discernible texture patterns on nonwoven webs are typically imparted to the nonwoven webs via processes like embossing, where the embossed texture is very regular and makes the textured or embossed nonwoven web exhibit a very engineered appearance, texture, and feel. The texture of such nonwoven webs has visual and tactile properties which make the structure less appealing than a more traditional woven web. Consumers desire nonwoven webs to have the appearance, tactile properties, and feel of more traditional woven materials as woven materials are viewed by consumers as being softer, with tactilely pleasing textures, and of high quality. As such, nonwoven webs should be improved to reflect more characteristics of woven materials.

SUMMARY

The present disclosure provides, in part, nonwoven webs with one or more repeat units that have the tactile properties, softness, and visual appears of woven fabrics. Stated differently, the nonwoven webs of the present disclosure provide a more clothlike feel and appearance compared to previous nonwovens.

A nonwoven web of the present disclosure may comprise a visually discernible pattern of three-dimensional features on a first surface or a second surface thereof, wherein the three-dimensional features may comprise regions with a plurality of irregular varying regions. These irregular varying regions provide for a variation in visual, tactile, and performance properties leading to the nonwoven webs being considered clothlike or woven material like. The performance of the nonwoven webs discussed herein is further driven to be woven-like and natural looking by also comprising regions of a plurality of substantially linear segments. These two different regions of the present disclosure provide for the natural type variation found in a woven material and consequently the nonwoven webs are viewed as having the visual, tactile, and performance properties of woven materials or woven, natural fabrics.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Various non-limiting forms of the present disclosure will now be described to provide an overall understanding of the principles of the structure, function, manufacture, and use of the nonwoven webs with one or more repeat units disclosed herein. One or more examples of these non-limiting forms are illustrated in the accompanying drawings. Those of ordinary skill in the art will understand that the nonwoven webs with one or more repeat units described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Prior to a discussion of the nonwoven webs with one or more repeat units, first absorbent articles and their features will be discussed as one possible use of the nonwoven webs. It will be understood that the nonwoven webs with one or more repeat units also have other uses in other products, such as in the medical field, the cleaning and/or dusting field, and/or the wipes field, for example.

General Description of an Absorbent Article

Figure 1:
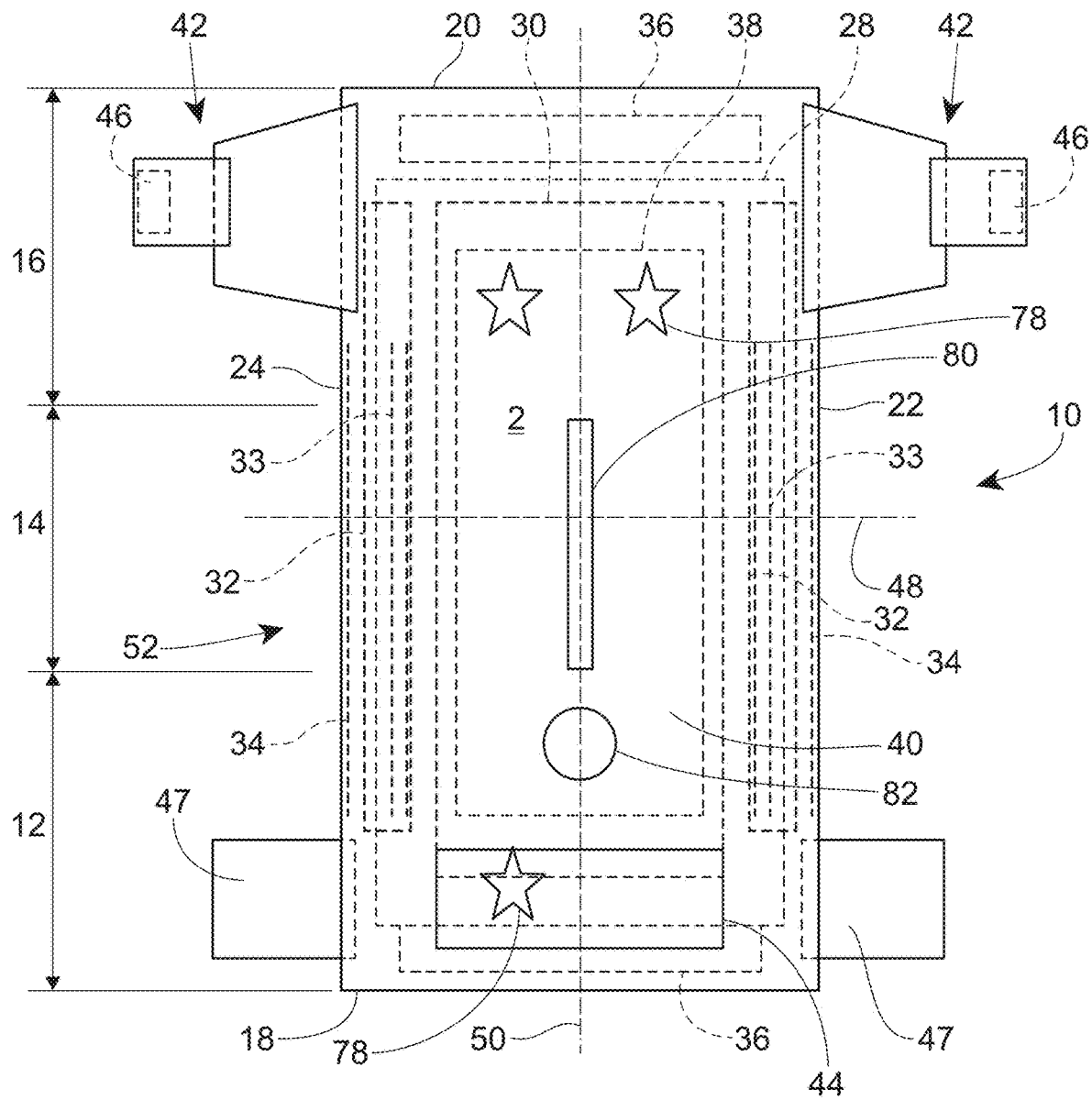
FIG. 1 is a plan view of an example absorbent article in the form of a taped diaper, garment-facing surface facing the viewer, in a flat laid-out state.
Figure 2:
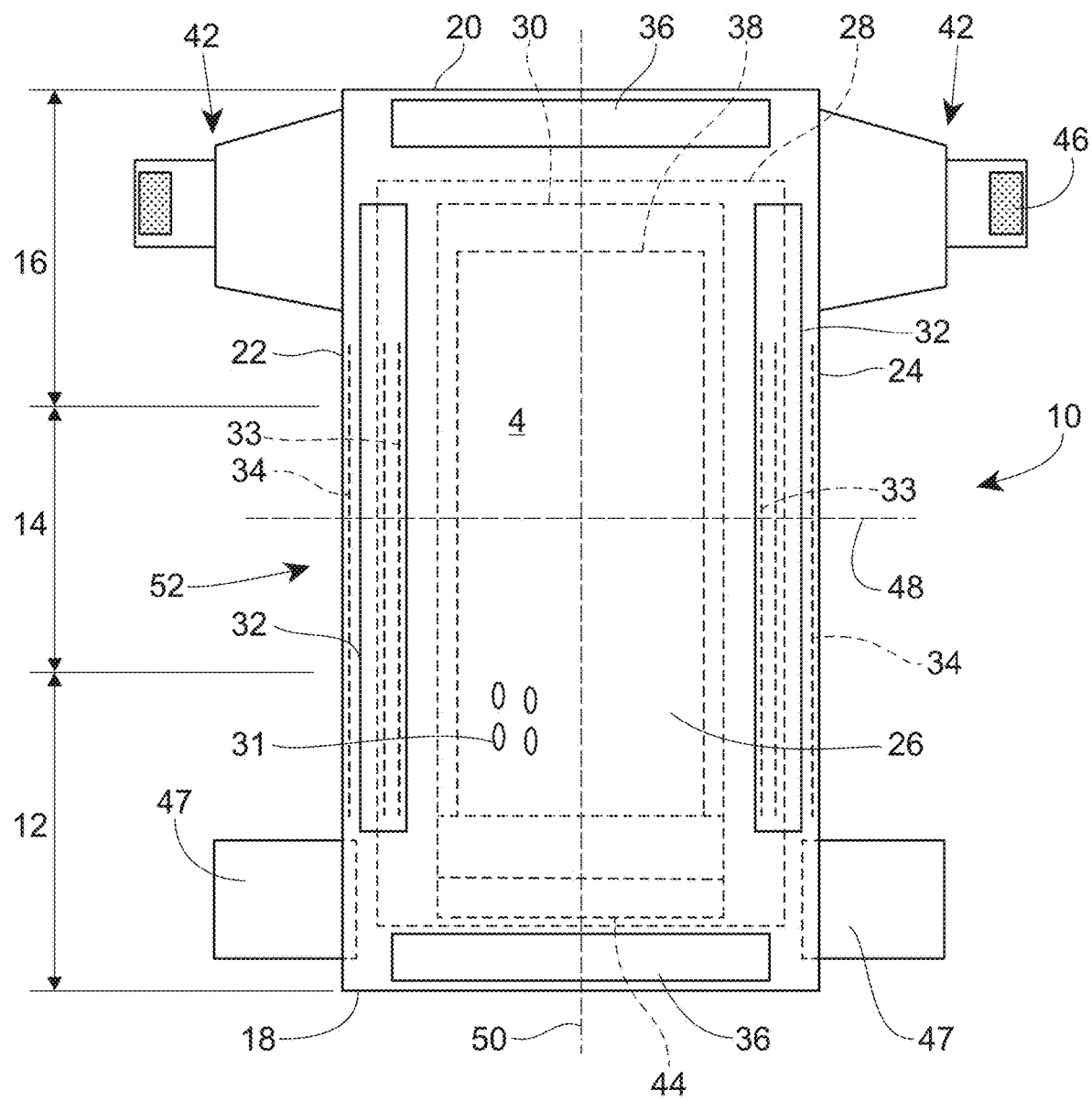
FIG. 2 is a plan view of the example absorbent article of FIG. 1, wearer-facing surface facing the viewer, in a flat laid-out state.
Figure 3:
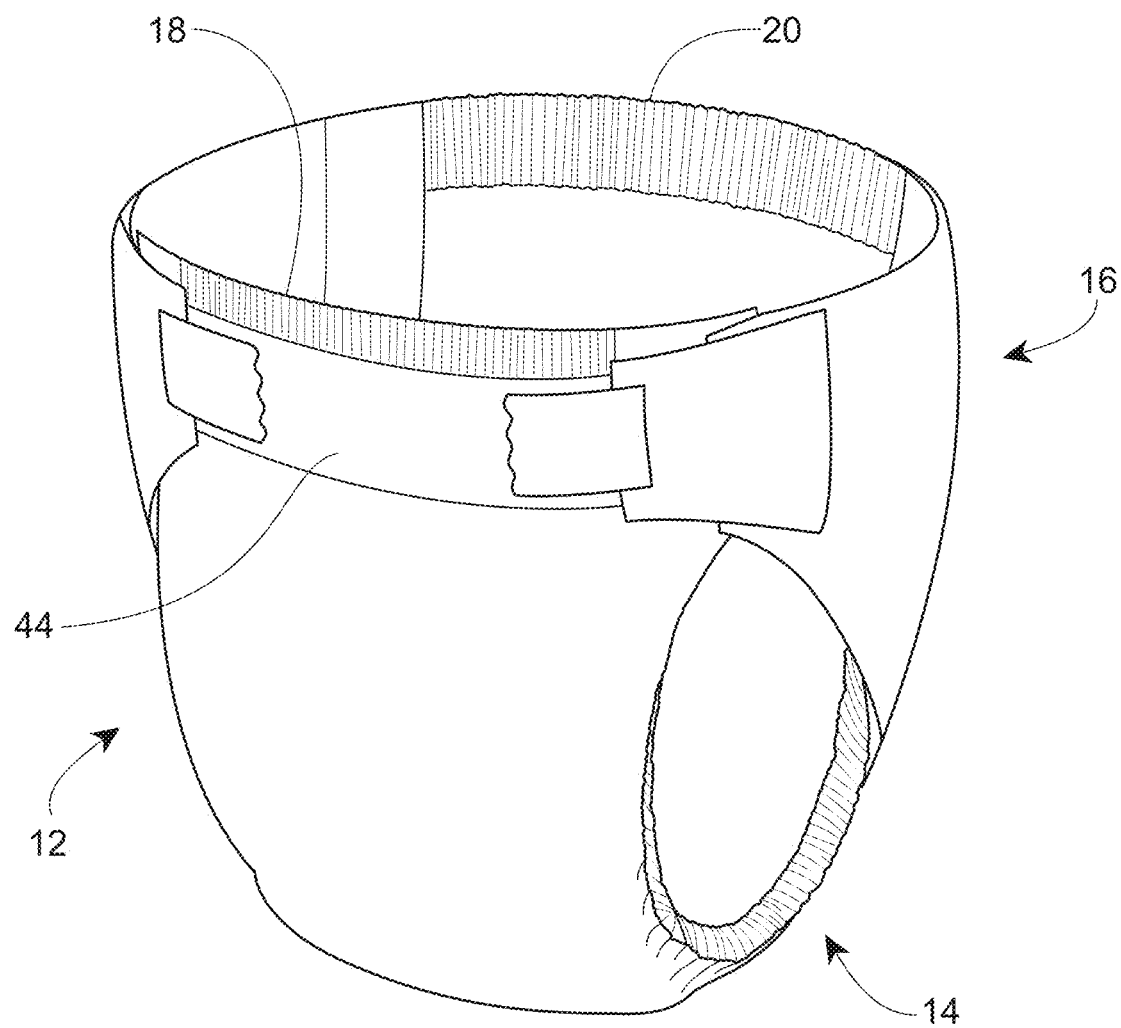
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover nonwoven material 40, such as a nonwoven web, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
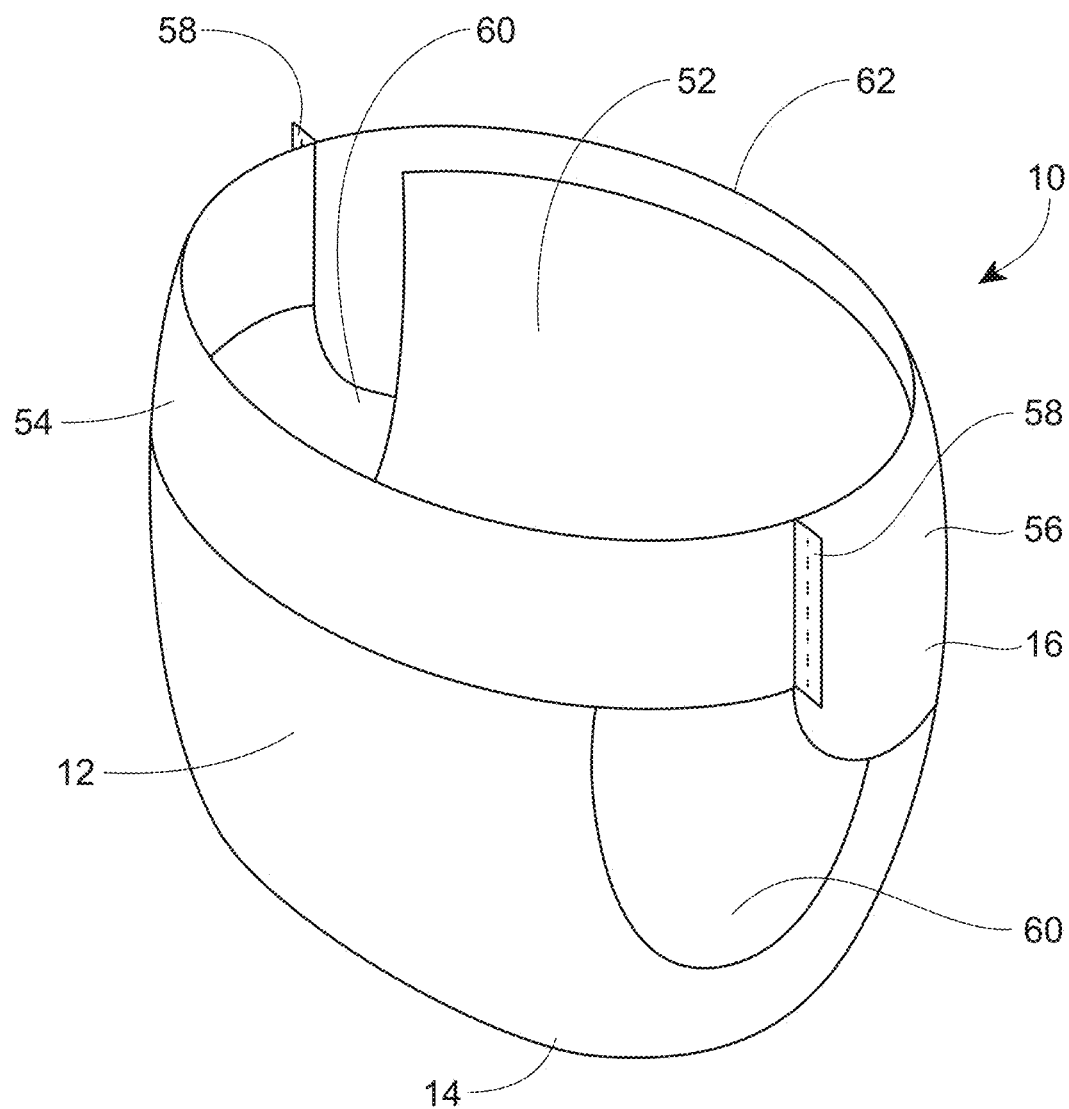
FIG. 4 is a front perspective view of an absorbent article in the form of a pant.
Figure 5:
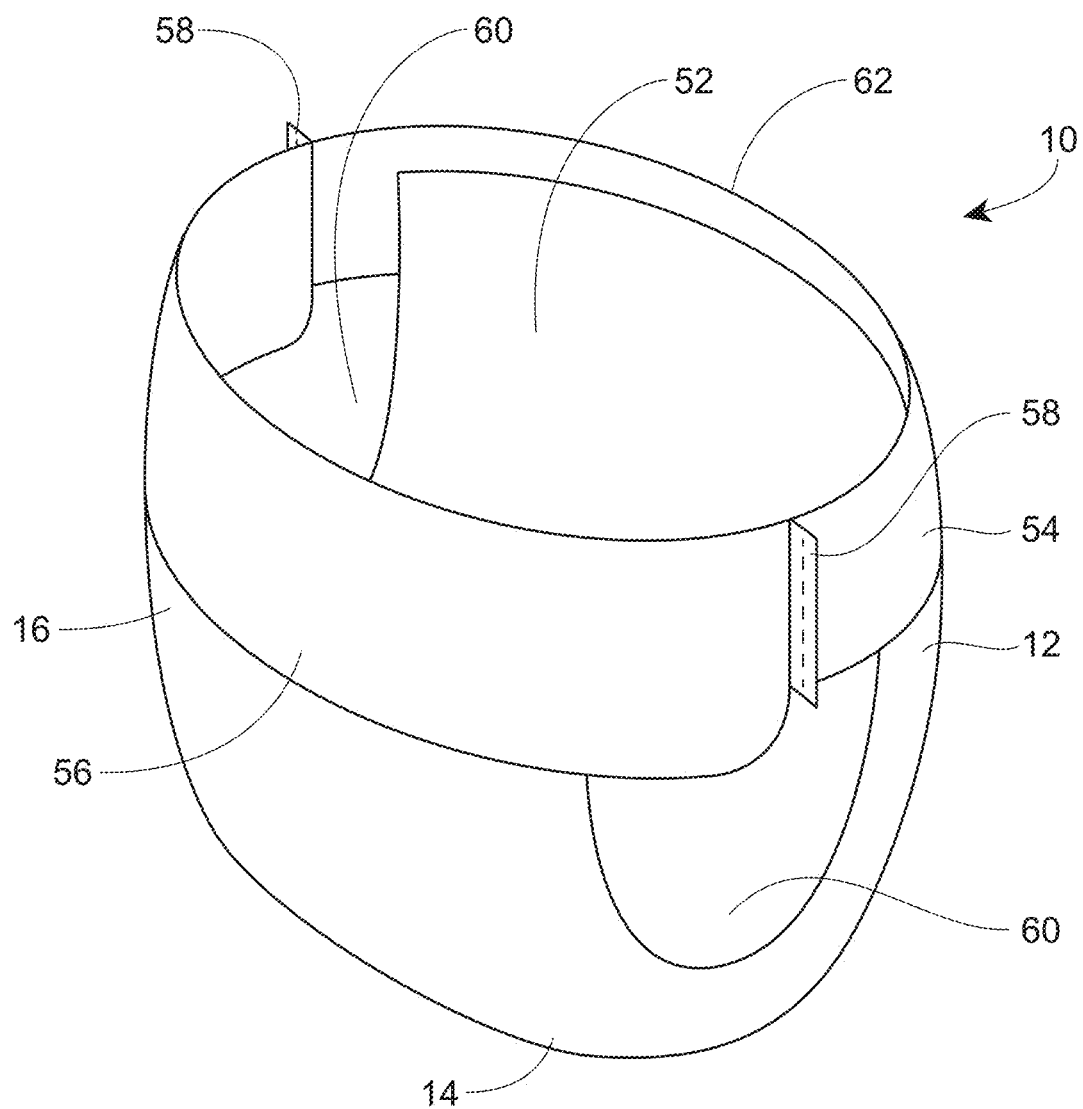
FIG. 5 is a rear perspective view of the absorbent article of FIG. 4.
Figure 6:
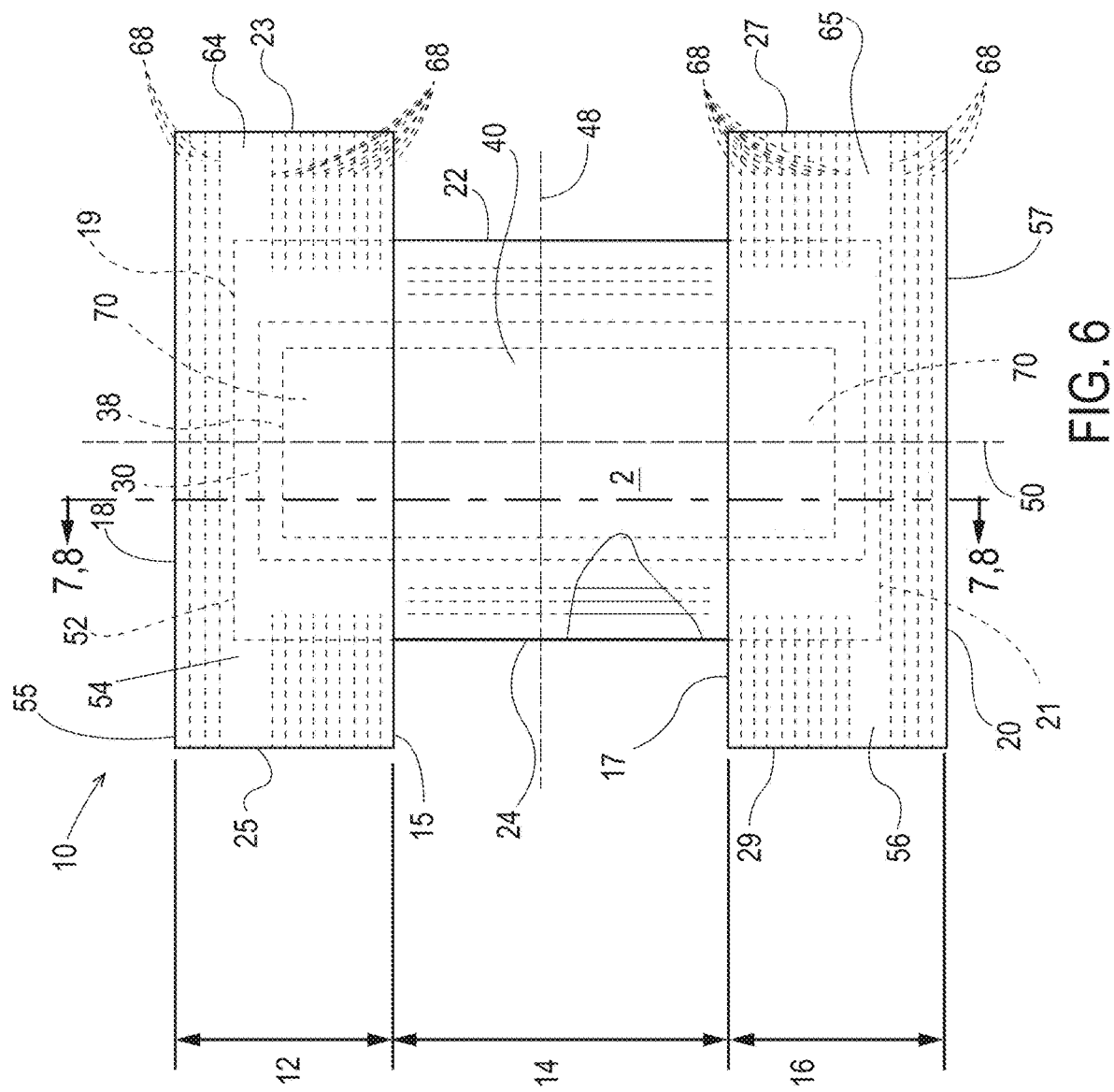
FIG. 6 is a plan view of the absorbent article of FIG. 4, laid flat, with a garment-facing surface facing the viewer.
Figure 7:
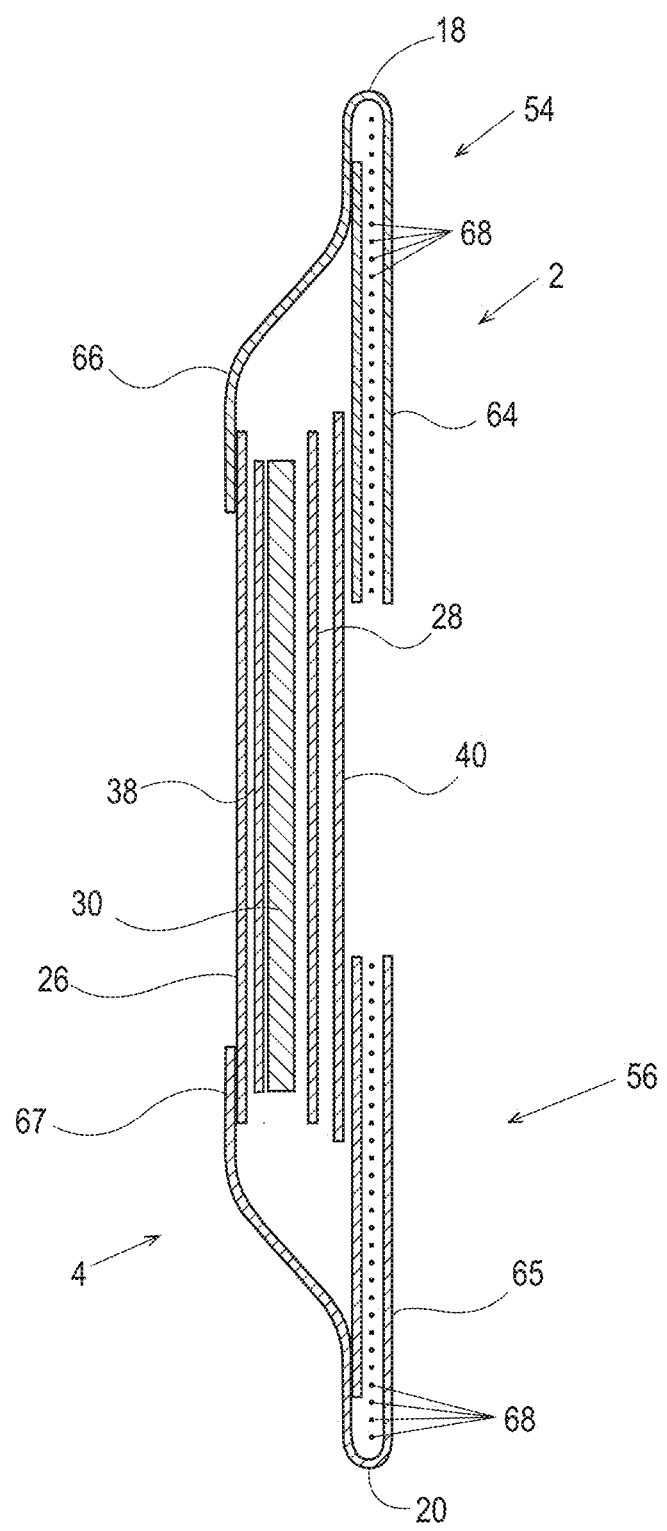
FIG. 7 is a cross-sectional view of the absorbent article taken about line 7-7 of FIG. 6.
Figure 8:
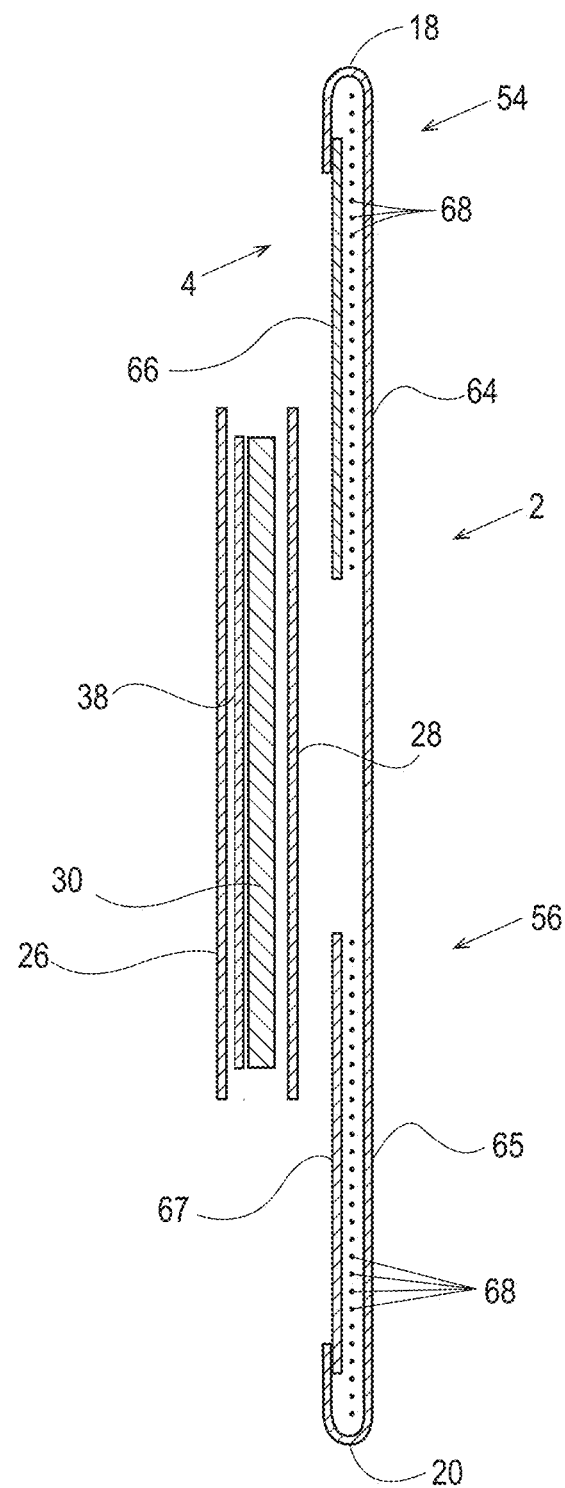
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24.

The nonwoven webs with the one or more repeat units may be used as nonwoven components of the belts.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven webs, woven or nonwoven webs of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 31), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The nonwoven webs with the one or more repeat units may be used as nonwoven topsheets.

Backsheet

The backsheet 28 is generally that portion of the absorbent article 10 positioned proximate to the garment-facing surface of the absorbent core 30. The backsheet 28 may be joined to portions of the topsheet 26, the outer cover nonwoven material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Nonwoven Material

The outer cover nonwoven material (sometimes referred to as a backsheet nonwoven) 40 may comprise one or more nonwoven materials joined to the backsheet 28 and that covers the backsheet 28. The outer cover nonwoven material 40 forms at least a portion of the garment-facing surface 2 of the absorbent article 10 and effectively "covers" the backsheet 28 so that film is not present on the garment-facing surface 2. The nonwoven webs with the one or more repeat units may be used as the outer cover nonwoven material.

Absorbent Core

Figure 9:
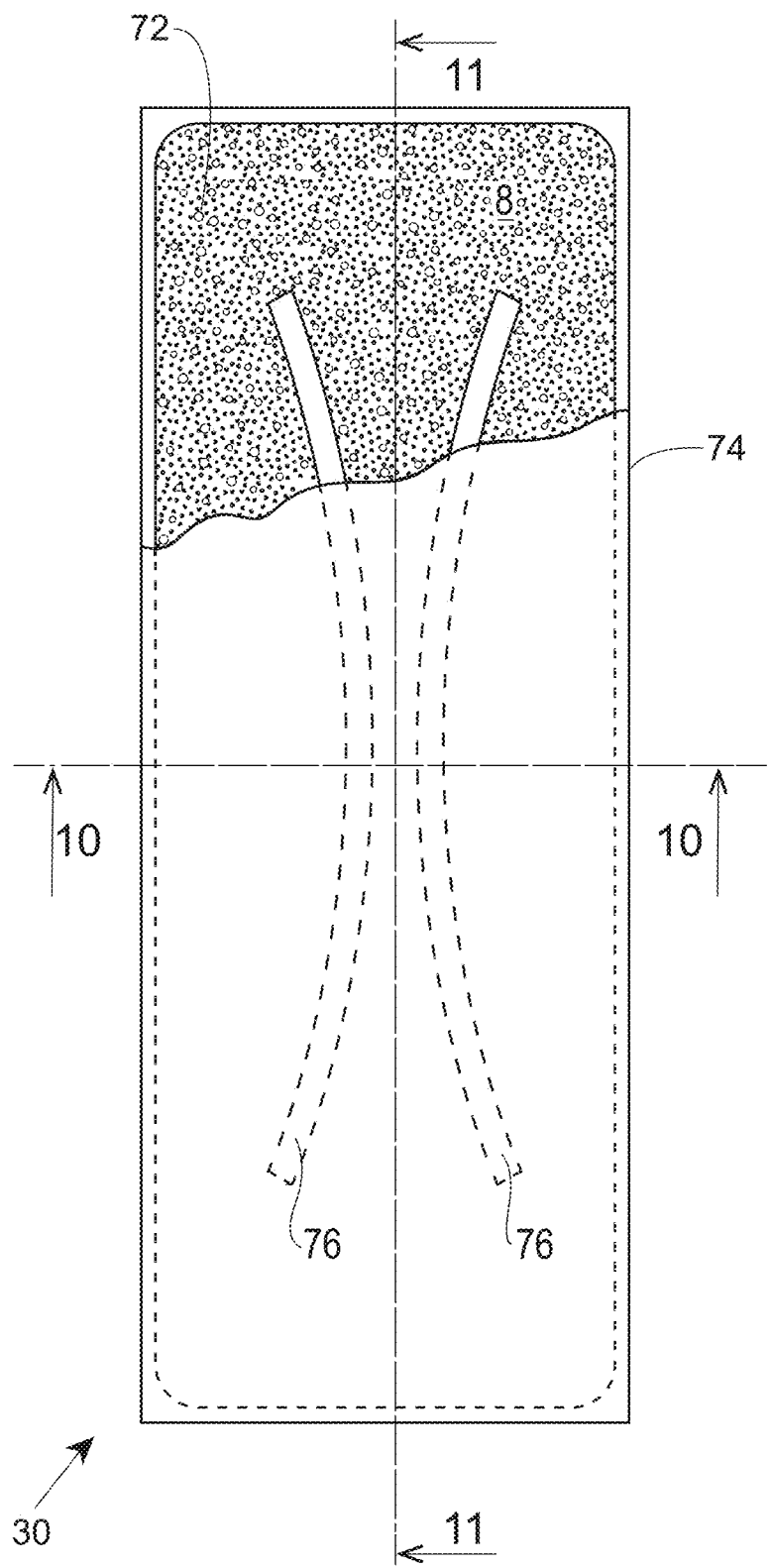
FIG. 9 is a plan view of an example absorbent core or an absorbent article.
Figure 10:
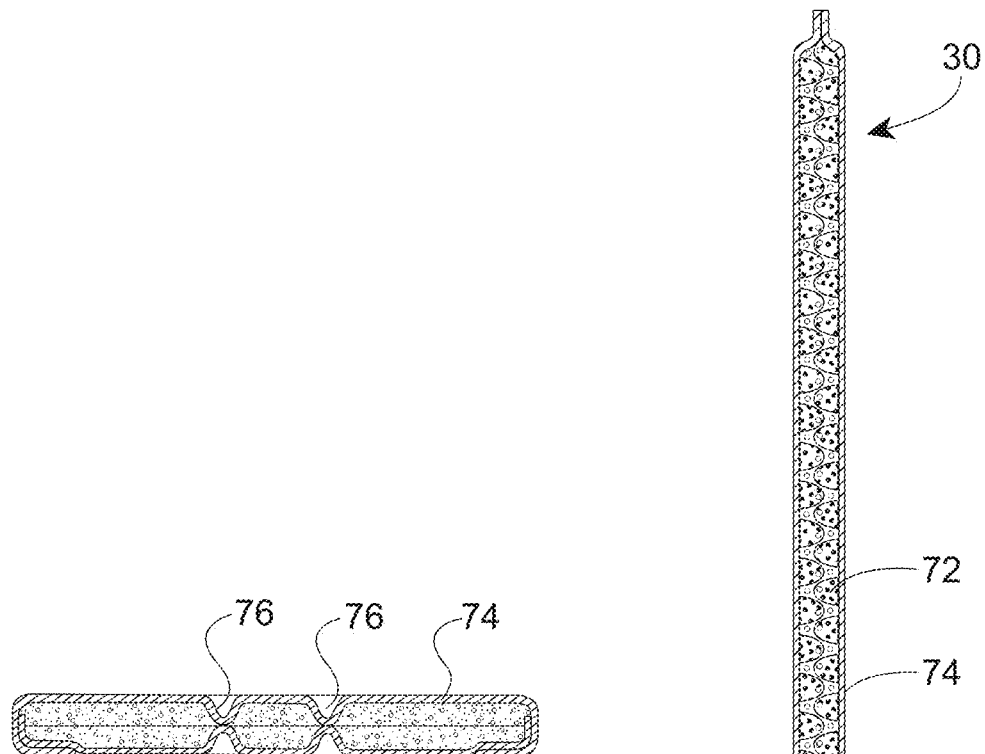
FIG. 10 is a cross-sectional view, taken about line 10-10, of the absorbent core of FIG. 9.
Figure 11:
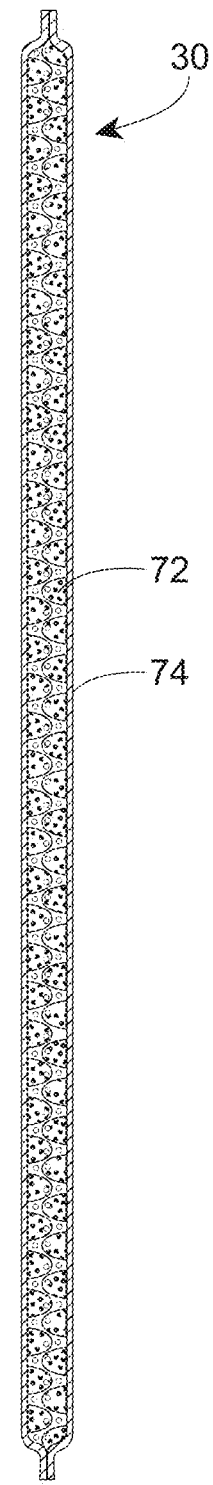
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material and may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

The nonwoven webs with the one or more repeat units may be used as nonwoven components of the barrier leg cuffs.

Waistband

Referring to FIGS. 1 and 2, the absorbent article 10 may comprise one or more elastic waistbands 36 or non-elastic waistband. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

The nonwoven webs with the one or more repeat units may be used as nonwoven components of the waistband.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven webs, foams, cellulosic materials, cross-linked cellulosic materials, air laid cellulosic nonwoven webs, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven web and as second acquisition material may comprise a cross-linked cellulosic material.

Landing Zone

Referring to FIGS. 1 and 2, the absorbent article 10 may have a landing zone area 44 that is formed in a portion of the garment-facing surface 2 of the outer cover nonwoven material 40. The landing zone area 44 may be in the back waist region 16 if the absorbent article 10 fastens from front to back or may be in the front waist region 12 if the absorbent article 10 fastens back to front.

In some instances, the landing zone 44 may be or may comprise one or more discrete nonwoven materials that are attached to a portion of the outer cover nonwoven material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

The nonwoven webs with the one or more repeat units may be used as nonwoven components of the landing zone.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven web and a second nonwoven web. The elastic film may or may not be apertured. The ears may be shaped. The ears may be integral (e.g., extension of the outer cover nonwoven material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

The nonwoven webs with the one or more repeat units may be used as nonwoven components of the front and back ears.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate number of absorbent articles per package. By packaging the absorbent articles under compression, caregivers can easily handle and store the packages, while also providing distribution savings to manufacturers owing to the size of the packages.

Sanitary Napkin

Figure 12:
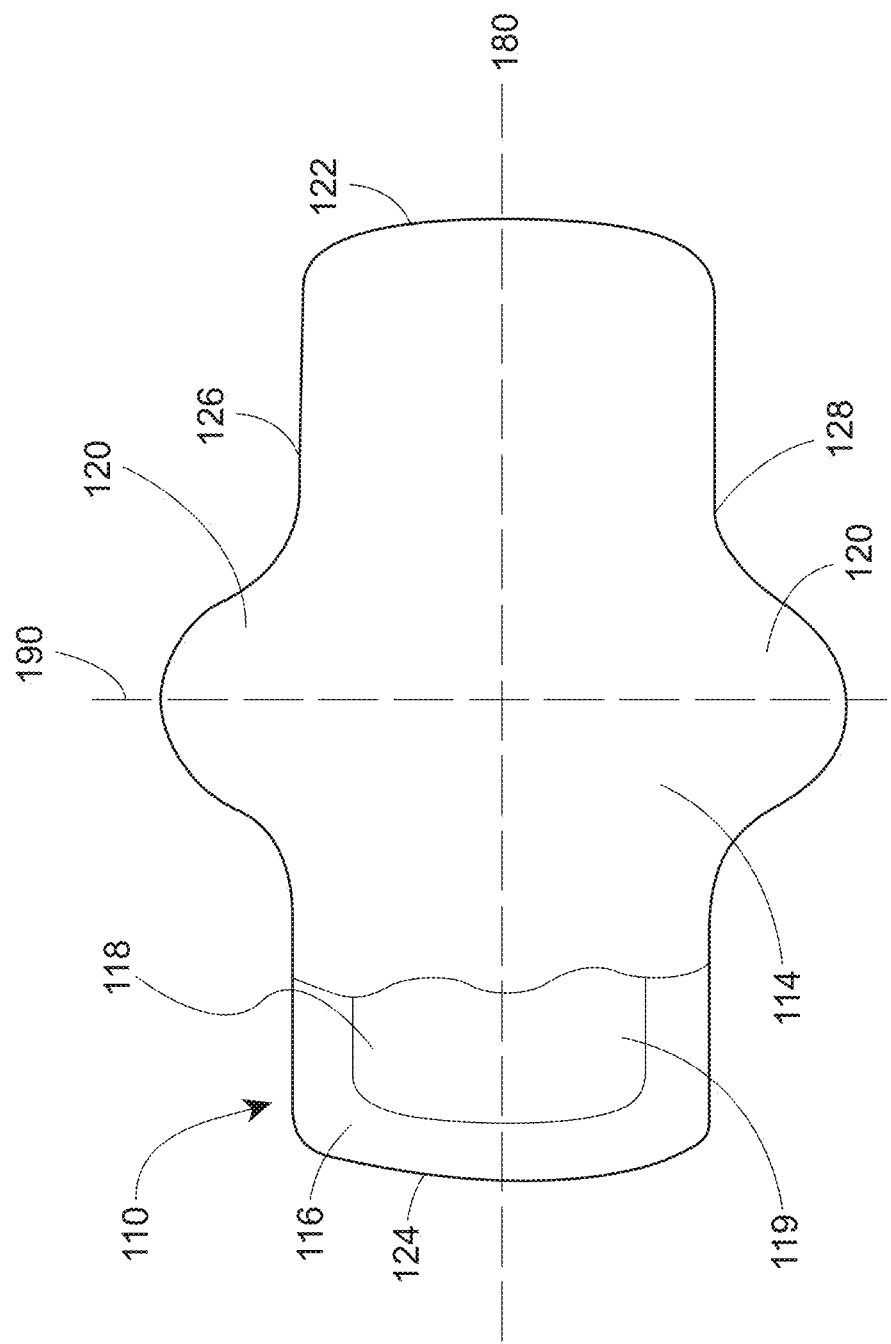
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

The nonwoven webs with one or more repeat units may be used as nonwoven components of sanitary napkins.

Nonwoven Webs with One or More Repeat Units

Figure 13:
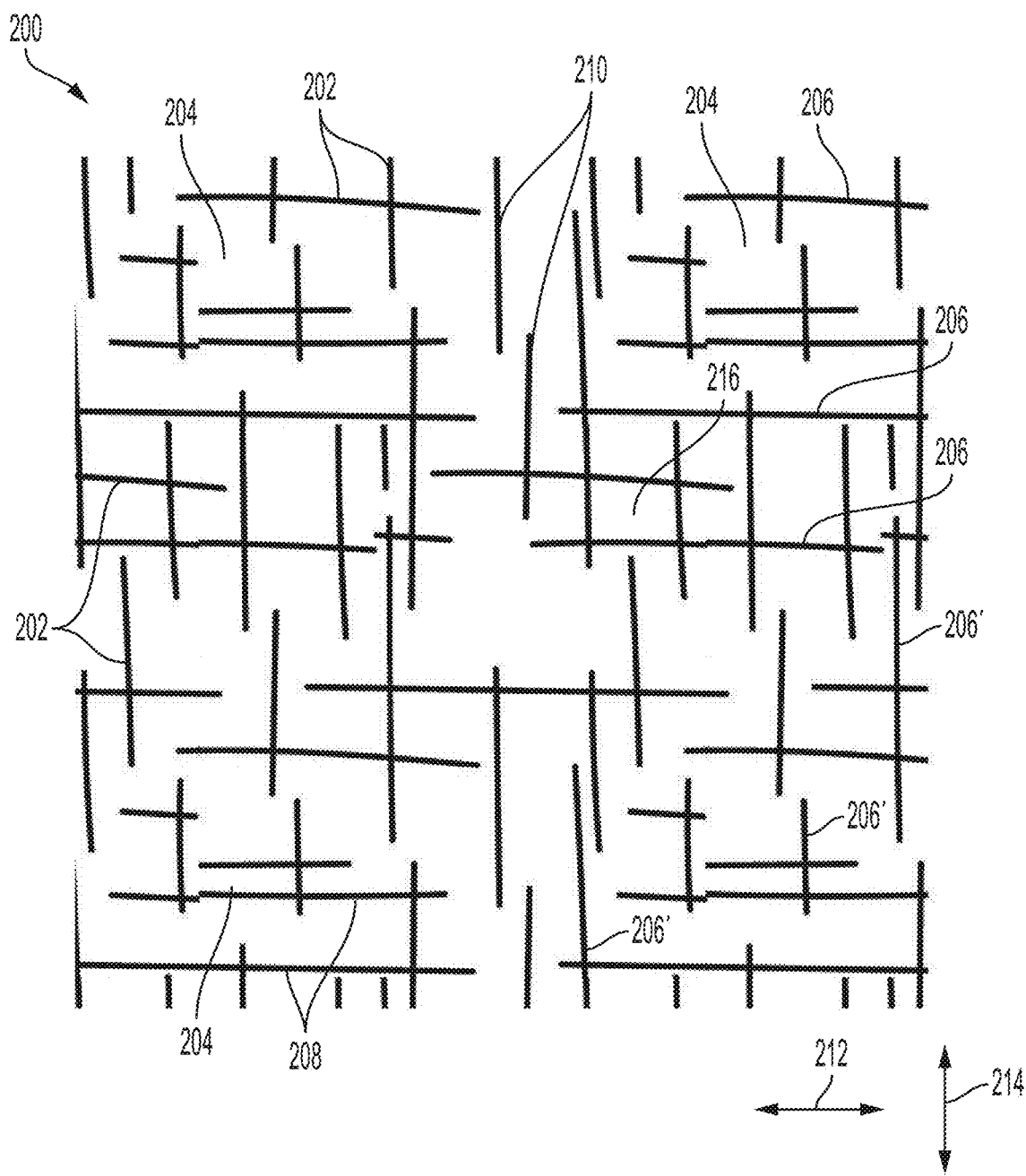
FIG. 13 is an example of a visually discernable pattern of three-dimensional features for a nonwoven web with a certain first region % area.
Figure 14:
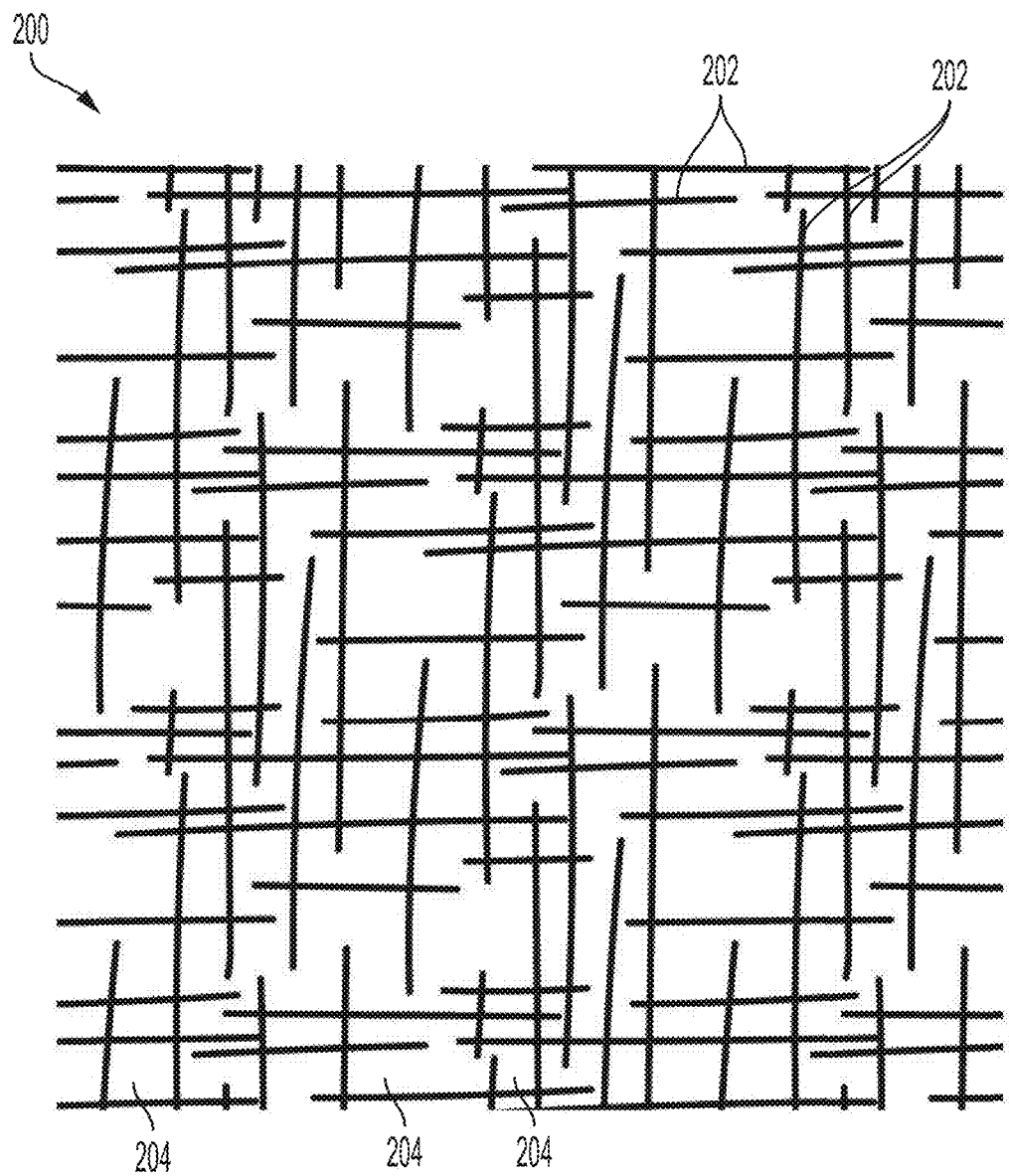
FIG. 14 is an example of a visually discernable pattern of three-dimensional features for a nonwoven web with a certain first region % area.
Figure 15:
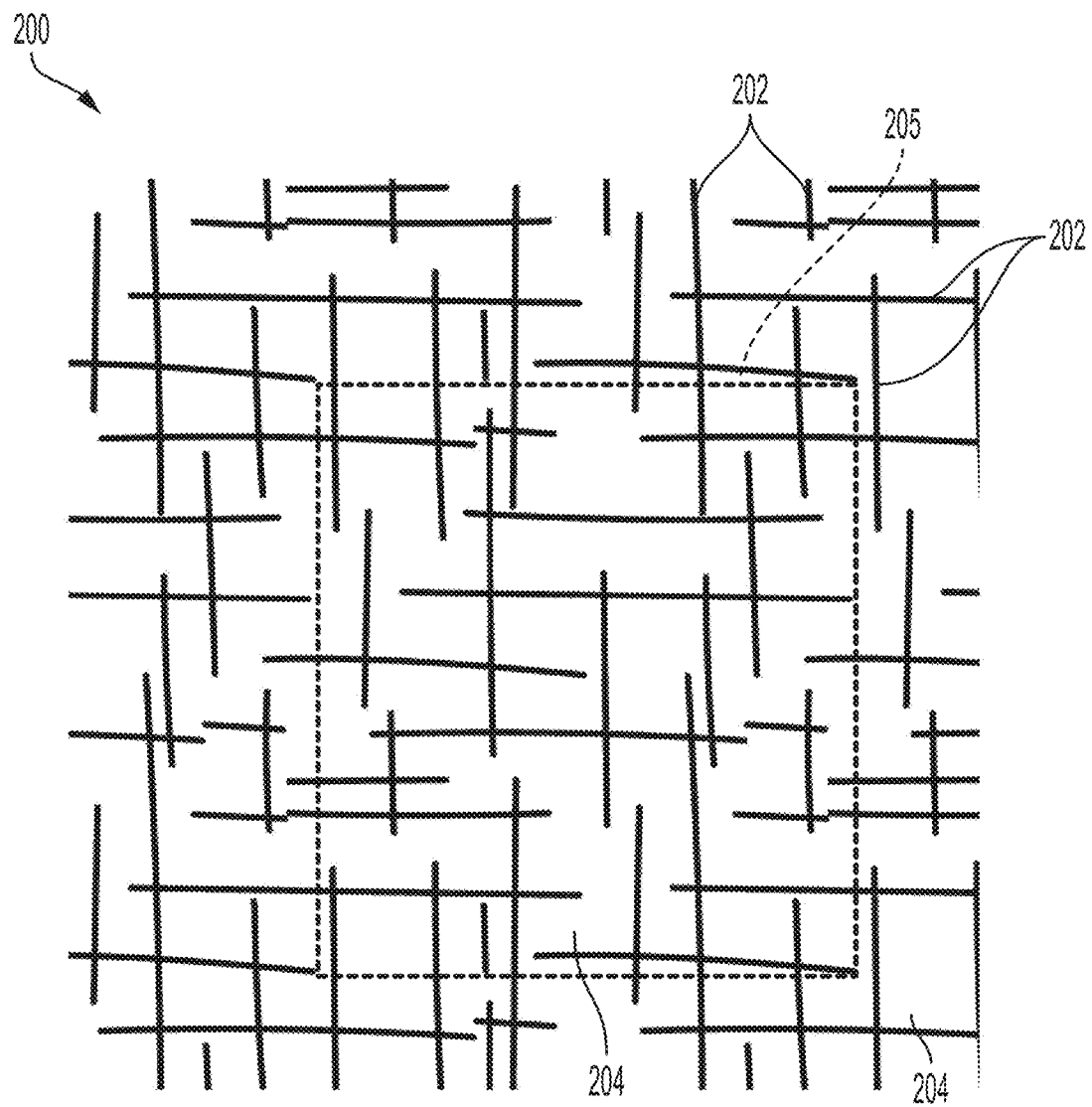
FIG. 15 is an example of a visually discernable pattern of three-dimensional features for a nonwoven web with a certain first region % area and showing a repeat unit.
Figure 16:
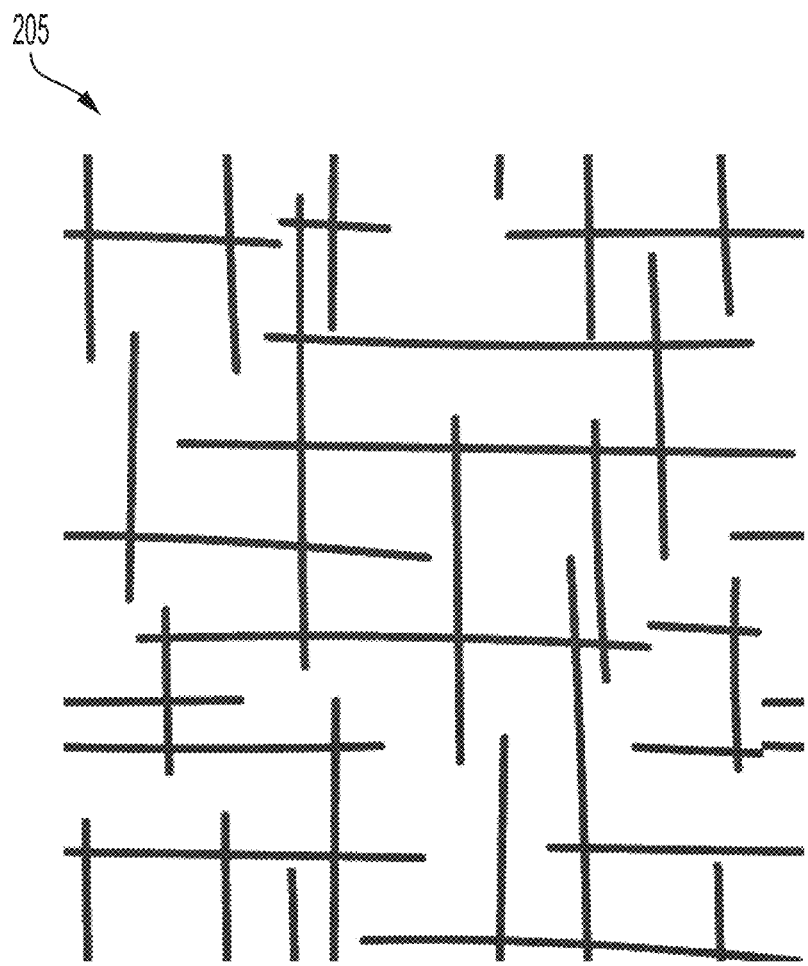
FIG. 16 illustrates the repeat unit of the visually discernable pattern of three-dimensional features of FIG. 15.
Figure 17:
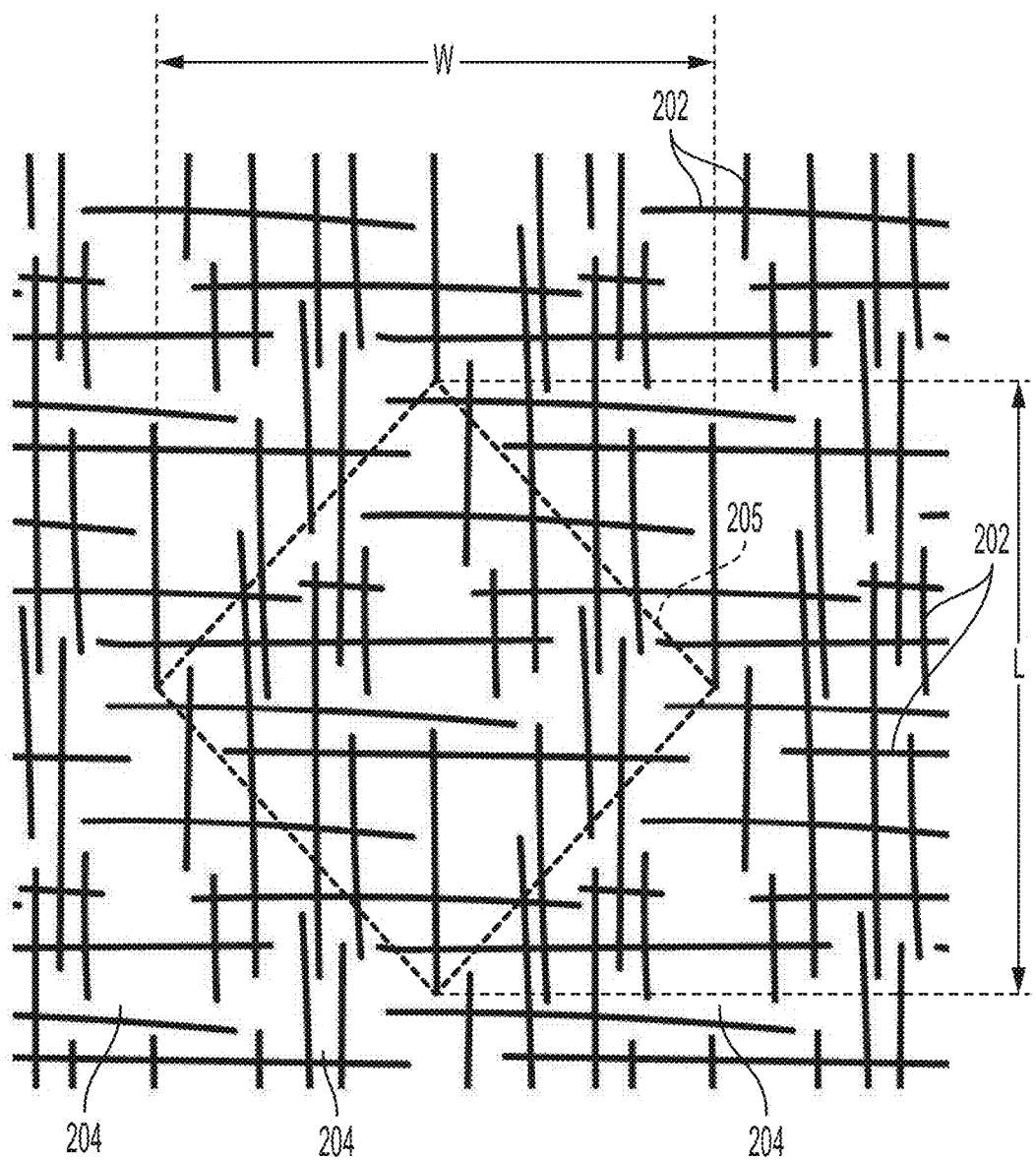
FIG. 17 is an example of a visually discernable pattern of three-dimensional features for a nonwoven web with a certain first region % area and showing a repeat unit.
Figure 18:
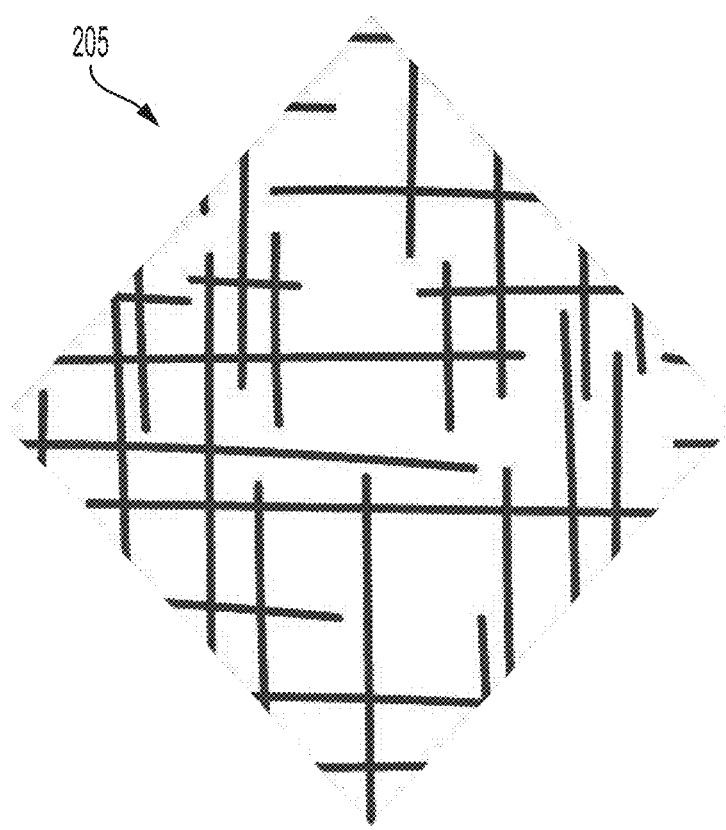
FIG. 18 illustrates the repeat unit of the visually discernable pattern of three-dimensional features of FIG. 17.
Figure 19:
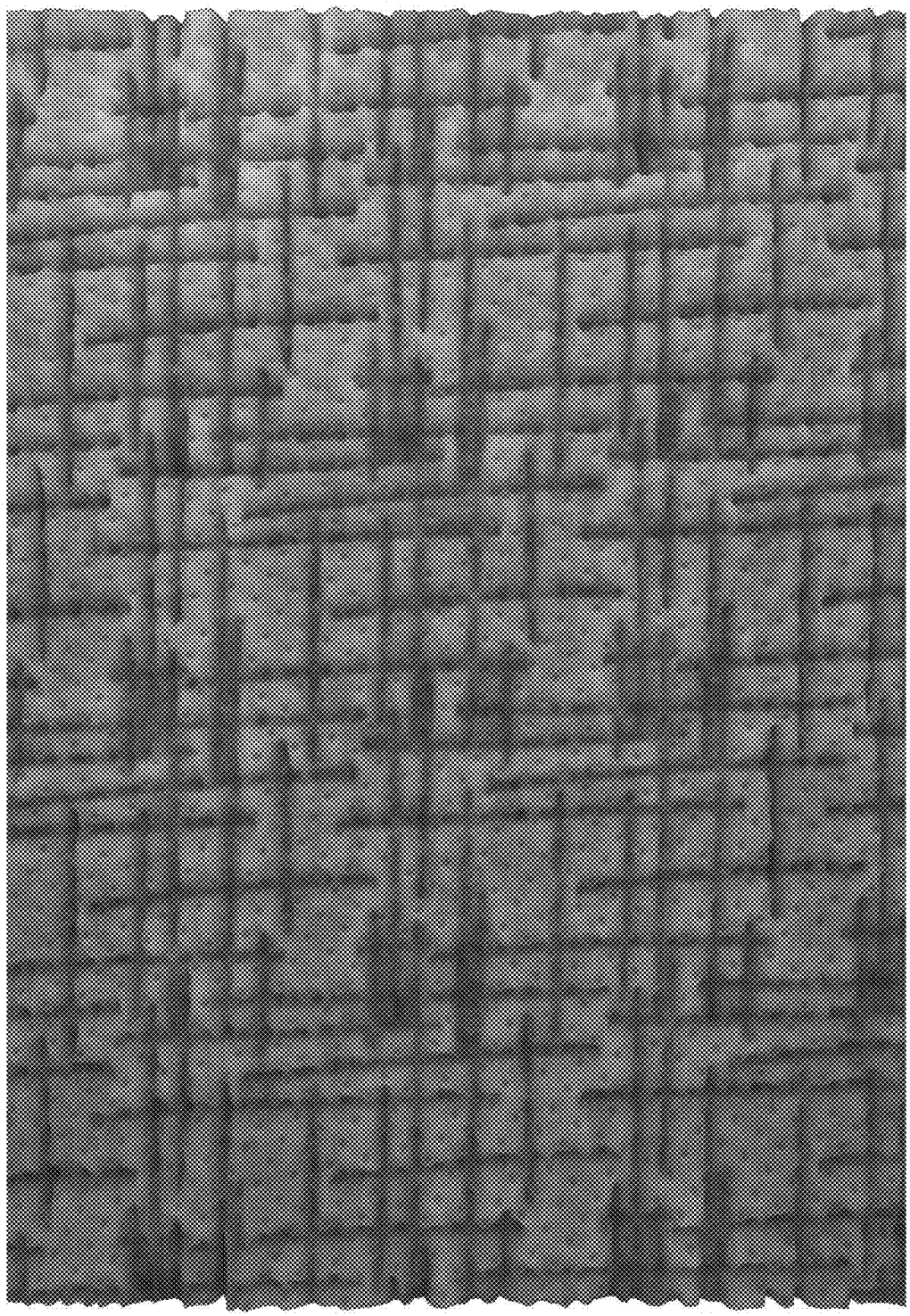
FIG. 19 is a photograph of a portion of a nonwoven web comprising a visually discernable pattern of three-dimensional features.

The nonwoven webs with one or more repeat units, or a plurality of repeat units are now discussed. FIG. 13 is an example of a visually discernable pattern of three-dimensional features for a nonwoven web with a certain first region % area. FIG. 14 is an example of a visually discernable pattern of three-dimensional features for a nonwoven web with a certain first region % area. FIG. 15 is an example of a visually discernable pattern of three-dimensional features for a nonwoven web with a certain first region % area and showing a repeat unit. FIG. 16 illustrates the repeat unit of the visually discernable pattern of three-dimensional features of FIG. 15. FIG. 17 is an example of a visually discernable pattern of three-dimensional features for a nonwoven web with a certain first region % area and showing a repeat unit. FIG. 18 illustrates the repeat unit of the visually discernable pattern of three-dimensional features of FIG. 17. FIG. 19 is a photograph of a portion of a nonwoven web comprising a visually discernable pattern of three-dimensional features.

The various visually discernable patterns of three-dimensional features 200 for nonwoven webs of FIGS. 13-19 may each comprise one or more first regions 202, or a plurality of first regions 202, and a plurality of second regions 204. The one or more first regions 202 may have a % area of about 5% to about 40%, about 8% to about 35%, about 8% to about 30%, about 10% to about 25%, or about 10% to about 20%, relative to an entire % area of the nonwoven web comprising the visually discernable pattern of three-dimensional features, specifically reciting all 0.1% increments within the specified ranges and all ranges formed therein or thereby. The plurality of second regions 204 may have a % area of about 60% to about 95%, about 65% to about 92%, about 70% to about 92%, about 75% to about 90%, or about 80% to about 90%, relative to the entire % area of the nonwoven web comprising the visually discernable pattern of three-dimensional features, specifically reciting all 0.1% increments within the specified ranges and all ranges formed therein or thereby. All % area measurements are according to the Pattern Analysis Test herein.

Referring to FIG. 13, the visually discernable pattern of three-dimensional features 200 for a nonwoven web may comprise one or more first regions 202, or a plurality of first regions 202, and a plurality of second regions 204. The one or more first regions 202 of FIG. 13 may have a area of about 11%, relative to an entire % area of the nonwoven web comprising the visually discernible pattern of three-dimensional features. The plurality of second regions 204 may have a area of about 89% relative to the entire % area of the nonwoven web comprising the visually discernible pattern of three-dimensional features. The sum of the % areas of the one or more first regions 202 and the plurality of the second regions 204 may add up to 100% or less, depending on the visually discernible pattern. In an instance when the sum is less than 100%, other features may be present, such as other three-dimensional features, for example.

Referring to FIG. 14, the visually discernable pattern of three-dimensional features 200 for a nonwoven web may comprise one or more first regions 202, or a plurality of first regions 202, and a plurality of second regions 204. The one or more first regions 202 of FIG. 14 may have a area of about 20%, relative to an entire % area of the nonwoven web comprising the visually discernible pattern of three-dimensional features. The plurality of second regions 204 may have a % area of about 80% relative to the entire % area of the nonwoven web comprising the visually discernible pattern of three-dimensional features. The sum of the % areas of the one or more first regions 202 and the plurality of the second regions 204 may add up to 100% or less, depending on the visually discernible pattern. In an instance when the sum is less than 100%, other features may be present, such as other three-dimensional features, for example.

Referring to FIG. 15, the visually discernable pattern of three-dimensional features 200 for a nonwoven web may comprise one or more first regions 202, or a plurality of first regions 202, and a plurality of second regions 204. The one or more first regions 202 of FIG. 15 may have a area of about 13%, relative to an entire % area of the nonwoven web comprising the visually discernible pattern of three-dimensional features. The plurality of second regions 204 may have a area of about 87% relative to the entire % area of the nonwoven web comprising the visually discernible pattern of three-dimensional features. The sum of the % areas of the one or more first regions 202 and the plurality of the second regions 204 may add up to 100% or less, depending on the visually discernible pattern. In an instance when the sum is less than 100%, other features may be present, such as other three-dimensional features, for example.

Referring to FIG. 17, the visually discernable pattern of three-dimensional features 200 for a nonwoven web may comprise one or more first regions 202, or a plurality of first regions 202, and a plurality of second regions 204. The one or more first regions 202 of FIG. 17 may have a area of about 18%, relative to an entire % area of the nonwoven web comprising the visually discernible pattern of three-dimensional features. The plurality of second regions 204 may have a area of about 82% relative to the entire % area of the nonwoven web comprising the visually discernible pattern of three-dimensional features. The sum of % areas of the one or more first regions 202 and the plurality of the second regions 204 may add up to 100% or less, depending on the visually discernible pattern. In an instance when the sum is less than 100%, other features may be present, such as other three-dimensional features, for example.

FIGS. 15 and 17 illustrate a repeat unit 205 in dash. The repeat units 205 are illustrated in FIGS. 16 and 18, respectively. Any nonwoven webs of the present disclosure may have one or more repeat units or a plurality of repeat units. If more than one repeat unit is provided, the repeat units may all be the same, slightly different, or different.

Referring again to FIG. 13, as an example, the one or more first regions 202, or the plurality of first regions 202, and the plurality of second regions 204 may be different. The one or more first regions 202 may comprise a plurality of substantially linear segments, a plurality of linear segments, and/or a plurality of substantially linear segments and a plurality of linear segments (hereinafter referred to herein as "substantially linear segments"). The plurality of second regions 204 may be free of, or substantially free of, the substantially linear segments. The plurality of substantially linear segments may comprise a first group 208 of the plurality of substantially linear segments 206 and at least a second group 210 of the plurality of substantially linear segments 206'. The first group 208 of the plurality of substantially linear segments 206 may intersect the second group 210 of the plurality of substantially linear segments 206' at angles of intersection. The angles of intersection may be in the range of about 60 degrees to about 120 degrees, about 70 degrees to about 110 degrees, about 80 degrees to about 100 degrees, or about 85 degrees to about 95 degrees, specifically reciting all 1 degree increments within the specified ranges and all ranges formed therein or thereby. In certain patterns, some angles of intersection may be different while other angles of intersection may be the same.

At least one of the substantially linear segments 206 of the first group 208 of the plurality of substantially linear segments may intersect at least two, at least 3, at least 4, at least 5, at least 6, but less than 15 of the substantially linear segments 206' of the second group 210 of the plurality of substantially linear segments. Likewise, at least one of the substantially linear segments 206' of the second group 210 of the plurality of substantially linear segments may intersect at least two, at least 3, at least 4, at least 5, at least 6, but less than 15, or less than 25, of the substantially linear segments 206 of the first group 208 of the plurality of substantially linear segments. The substantially linear segments 206 in the first group 208 of the plurality of substantially linear segments may extend in a first direction 212, or within about 0.1 degrees to about 20 degrees, about 0.1 degrees to about 15 degrees, or about 0.1 degrees to about 10 degrees, from the first direction 212, specifically reciting all 0.1 degree increments within the specified ranges and all ranges formed therein or thereby. The substantially linear segments 206' in the second group 210 of the plurality of linear segments may extend in a second, different direction 214, or within about 0.1 degrees to about 20 degrees, about 0.1 degrees to about 15 degrees, or about 0.1 degrees to about 10 degrees from the second direction 214, specifically reciting all 0.1 degree increments within the specified ranges and all ranges formed therein or thereby. The first direction 212 may be perpendicular to the second direction 214. The substantially linear segments 206 in the first group 208 may extend in different directions, although still extending generally about the first direction 212. Likewise, the substantially linear segments 206' in the second group 208 may extend in different directions, although still extending generally about the second direction 214.

Still referring to FIG. 13, the substantially linear segments 206 in the first group 208 may have a plurality of different lengths along the first direction 212, although some of the substantially linear segments 206 may have the same length. The substantially linear segments 206' in the second group 210 may have a plurality of different lengths along the second direction 214, although some of the substantially linear segments 206' may have the same length. It is envisioned that some of the substantially linear segments 206 in the first group 208 may have the same length as some of the substantially linear segments 206' in the second group 210. The lengths of the substantially linear segments in the first and second groups may be in the range about 2 mm to about 100 mm, about 2 mm to about 80 mm, about 2 mm to about 60 mm, about 2 mm to about 50 mm, about 2 mm to about 45 mm, or about 3 mm to about 40 mm, specifically reciting all 0.1 mm increments within the specified ranges and all ranges formed therein or thereby. The substantially linear segments 206 in the first group 208 may have the same widths or different widths. Likewise, the substantially linear segments 206' in the second group 210 may have the same widths or different widths. The width(s) of the substantially linear segments 206 of the first group 208 may be the same as or different than the width(s) of the substantially linear segments 206' of the second group 210. The widths of the substantially linear segments 206 and 206' may be in the range of about 0.5 mm to about 3 mm, specifically reciting all 0.1 mm increments within the specified range.

At least some of the one or more first regions 202 may fully enclose or surround a second region 204 to form an enclosed second region 216. At least some of the plurality of second regions 204 may form a peninsular shape.

The above descriptions with respect to FIG. 13 may also apply to FIGS. 14-19. The nonwoven webs comprising the visually discernable patterns of three-dimensional elements may have a basis weight in the range of about 10 gsm to about 100 gsm, about 10 gsm to about 60 gsm, about 15 gsm to about 50 gsm, about 15 gsm to about 45 gsm, about 20 gsm to about 40 gsm, about 20 gsm to about 35 gsm, about 20 gsm to about 30 gsm, according to the Basis Weight Test herein, and specifically reciting all 0.1 gsm increments within the specified ranges and all ranges formed therein or thereby.

The visually discernable pattern of three-dimensional elements may be formed in a nonwoven web by embossing, hydroentangling, or by using a structured forming belt for fiber laydown. Using embossing or hydroentangling, the first regions or the second regions may be embossed or hydroentangled to form the pattern. The structured forming belt will be discussed further below. The nonwoven webs may form a nonwoven component of an absorbent article or other consumer products, such a cleaning or dusting product, or a wipe, for example. The absorbent article (as discussed above) may comprise a liquid permeable topsheet, a liquid impermeable backsheet, and an absorbent core positioned at least partially intermediate the topsheet and the backsheet. The absorbent article may also comprise an outer cover nonwoven material in a facing relationship with the backsheet and forming a garment-facing surface of the absorbent article. The nonwoven webs comprising the visually discernible pattern of three-dimensional features 200 may form a topsheet, or portion thereof, an outer cover nonwoven material, or portion thereof, a portion of a wing, a portion of an ear, a portion of a belt, a portion of leg cuff, or a portion of a waistband, for example. The nonwoven webs may also form more than one component of an absorbent article or other consumer product. The nonwoven webs may also be used in medical gowns, wound dressings, and/or other medical products comprising nonwoven components.

Irregular Varying Regions

The plurality of second regions 204 of a visually discernable pattern of three-dimensional features 200 on a nonwoven web may comprise about 5 to about 150, about 10 to about 100, about 10 to about 50, about 10 to about 40, or about 10 to about 30, irregular varying regions, according to the Pattern Analysis Test herein, specifically reciting all 1 increments within the specified ranges and all ranges formed therein or thereby. The irregular varying regions may vary in shape and/or area.

These irregular varying regions create the impression of a natural, organic, or woven nonwoven web, which is consumer desirable. These irregular varying regions provide for a variation in visual, tactile, and performance properties leading to the nonwoven webs being considered clothlike or woven material like.

Area Variability

The plurality of second regions 204 of a visually discernable pattern of three-dimensional features 200 on a nonwoven web may have an Area Variability of greater than 50%, but less than 150%, of greater than 70%, but less than 140%, of greater than 80%, but less than 130%, or of greater than 85%, but less than 125%, according to the Pattern Analysis Test herein, specifically reciting all 1% increments within the specified ranges and all ranges formed therein or thereby.

The area variability of the second regions create the impression of a natural, organic, or woven nonwoven web, which is consumer desirable. The area variability of the second regions provide for a variation in visual, tactile, and performance properties leading to the nonwoven webs being considered clothlike or woven material like.

Shape Variability

The plurality of second regions 204 of a visually discernable pattern of three-dimensional features 200 on a nonwoven web may have an Shape Variability of greater than 20%, but less than 120%, of greater than 30%, but less than 110%, of greater than 35%, but less than 110%, or of greater than 40%, but less than 100%, according to the Pattern Analysis Test herein, specifically reciting all 1% increments within the specified ranges and all ranges formed therein or thereby.

The shape variability of the second regions create the impression of a natural, organic, or woven nonwoven web, which is consumer desirable. The shape variability of the second regions provide for a variation in visual, tactile, and performance properties leading to the nonwoven webs being considered clothlike or woven material like.

Materials

The nonwoven webs of the present disclosure may be formed by a dry-laid process using short staple fibers and mechanical web formation, such as a carding process. The resulting webs may be bonded using irregular pattern thermal embossing or hydroforming/hydroentangling processes. The nonwoven webs may also comprise cotton or other natural fibers. The nonwoven webs of the present disclosure may also be coform webs. Coformed webs typically comprise a matrix of meltblown fibers mixed with at least one additional fibrous organic materials, such as fluff pulp, cotton, and/or rayon, for example. The coform webs may be further structured by embossing or laying down the composite on a structured belt during a coforming process. In an instance, continuous spunbond filaments are used in producing the nonwoven webs if the nonwoven webs are being made on a structured forming belt (as described below). The nonwoven webs may comprise continuous mono-component polymeric filaments comprising a primary polymeric component. The nonwoven webs may comprise continuous multicomponent polymeric filaments comprising a primary polymeric component and a secondary polymeric component. The filaments may be continuous bicomponent filaments comprising a primary polymeric component A and a secondary polymeric component B, The bicomponent filaments have a cross-section, a length, and a peripheral surface. The components A and B may be arranged in substantially distinct zones across the cross-section of the bicomponent filaments and may extend continuously along the length of the bicomponent filaments. The secondary component B constitutes at least a portion of the peripheral surface of the bicomponent filaments continuously along the length of the bicomponent filaments. The polymeric components A and B may be melt spun into multicomponent fibers on conventional melt spinning equipment. The equipment may be chosen based on the desired configuration of the multicomponent. Commercially available melt spinning equipment is available from Hills, Inc. located in Melbourne, Fla. The temperature for spinning is in the range of about 110° C. to about 230° C. The bicomponent spunbond filaments may have an average diameter from about 6 microns to about 40 microns or from about 12 microns to about 40 microns, for example.

Figure 20A:
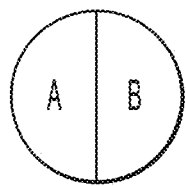
FIG. 20A is a schematic drawing illustrating a cross-section of a filament made with a primary component A and a secondary component B in a side-by-side arrangement.
Figure 20B:
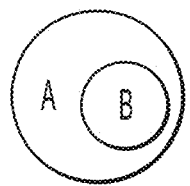
FIG. 20B is a schematic drawing illustrating a cross-section of a filament made with a primary component A and a secondary component B in an eccentric sheath/core arrangement.
Figure 20C:
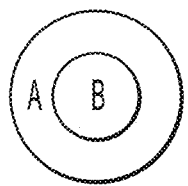
FIG. 20C is a schematic drawing illustrating a cross-section of a filament made with a primary component A and a secondary component B in a concentric sheath/core arrangement.
Figure 21:
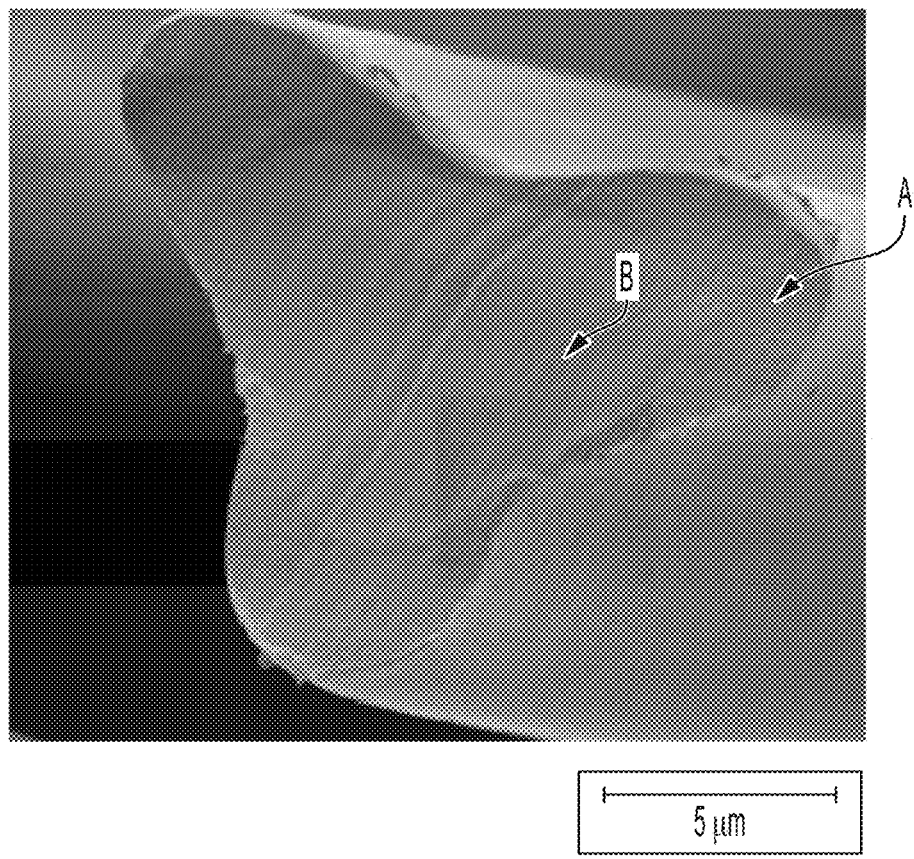
FIG. 21 is a perspective view photograph of a tri-lobal, bicomponent fiber.

The components A and B may be arranged in either a side-by-side arrangement as shown in FIG. 20A or an eccentric sheath/core arrangement as shown in FIG. 20B to obtain filaments which exhibit a natural helical crimp. Alternatively, the components A and B may be arranged in a concentric sheath/core arrangement as shown in FIG. 20C. Additionally, the component A and B may be arranged in multi-lobal sheath/core arrangement as shown in FIG. 21. Other multicomponent fibers may be produced by using the compositions and methods of the present disclosure. The bicomponent and multicomponent fibers may be segmented pie, ribbon, islands-in-the-sea configurations, or any combination thereof. The sheath may be continuous or non-continuous around the core. The fibers of the present disclosure may have different geometries that comprise round, elliptical, star shaped, rectangular, and other various geometries. Methods for extruding multicomponent polymeric filaments into such arrangements are generally known to those of ordinary skill in the art.

A wide variety of polymers are suitable for the nonwoven webs of the present disclosure including polyolefins (such as polyethylene, polypropylene and polybutylene), polyesters, polyamides, polyurethanes, elastomeric materials, and the like. Examples of polymer materials that may be spun into filaments may comprise natural polymers.

Primary component A and secondary component B may be selected so that the resulting bicomponent filament provides improved nonwoven bonding and softness. Primary polymer component A may have melting temperature which is lower than the melting temperature of secondary polymer component B.

Primary polymer component A may comprise polyethylene, polypropylene or random copolymer of propylene and ethylene. Secondary polymer component B may comprise polypropylene or random copolymer of propylene and ethylene. Polyethylenes may comprise linear low density polyethylene and high density polyethylene. In addition, secondary polymer component B may comprise polymers, additives for enhancing the natural helical crimp of the filaments, lowering the bonding temperature of the filaments, and enhancing the abrasion resistance, strength and softness of the resulting fabric.

Inorganic fillers, such as the oxides of magnesium, aluminum, silicon, and titanium, for example, may be added as inexpensive fillers or processing aides. Pigments and/or color melt additives may also be added.

The fibers of the nonwoven webs disclosed herein may comprise a slip additive in an amount sufficient to impart the desired haptics to the fiber. As used herein, "slip additive" or "slip agent" means an external lubricant. The slip agent when melt-blended with the resin gradually exudes or migrates to the surface during cooling or after fabrication, hence forming a uniform, invisibly thin coating, thereby yielding permanent lubricating effects. The slip agent may be a fast bloom slip agent.

During the making or in a post-treatment or even in both, the nonwoven webs of the present disclosure may be treated with surfactants or other agents to either hydrophilize the web or make it hydrophobic. For example, a nonwoven web used as a topsheet may be treated with a hydrophilizing material or surfactant so as to make it permeable to body exudates, such as urine and menses. For other absorbent articles, the nonwoven webs may remain in their naturally hydrophobic state or made even more hydrophobic through the addition of a hydrophobizing material or surfactant.

Suitable materials for preparing the multicomponent filaments of the nonwoven webs of the present disclosure may comprise PP3155 polypropylene obtained from Exxon Mobil Corporation and PP3854 polypropylene obtained from Exxon Mobil Corporation.

Structured Forming Belts and Process for Producing Nonwoven Webs

As mentioned above, the nonwoven webs of the present disclosure may be produced by embossing, hydroentangling, or by using a structured forming belt for fiber or filament laydown. The structured forming belt and the process of manufacture will be described now. The nonwoven webs may be formed directly on the structured forming belt with continuous spunbond filaments in a single forming process. The nonwoven webs may assume a shape and texture which corresponds to the shape and texture of the structured forming belt.

The present disclosure may utilize the process of melt spinning. Melt spinning may occur from about 150° C. to about 280° or from about 190° to about 230°, for example. Fiber spinning speeds may be greater than 100 meters/minute, from about 1,000 to about 10,000 meters/minute, from about 2,000 to about 7,000 meters/minute, or from about 2,500 to about 5,000 meters/minute, for example. Spinning speeds may affect the brittleness of the spun fiber, and, in general, the higher the spinning speed, the less brittle the fiber. Continuous fibers may be produced through spunbond methods or meltblowing processes.

Figure 22:
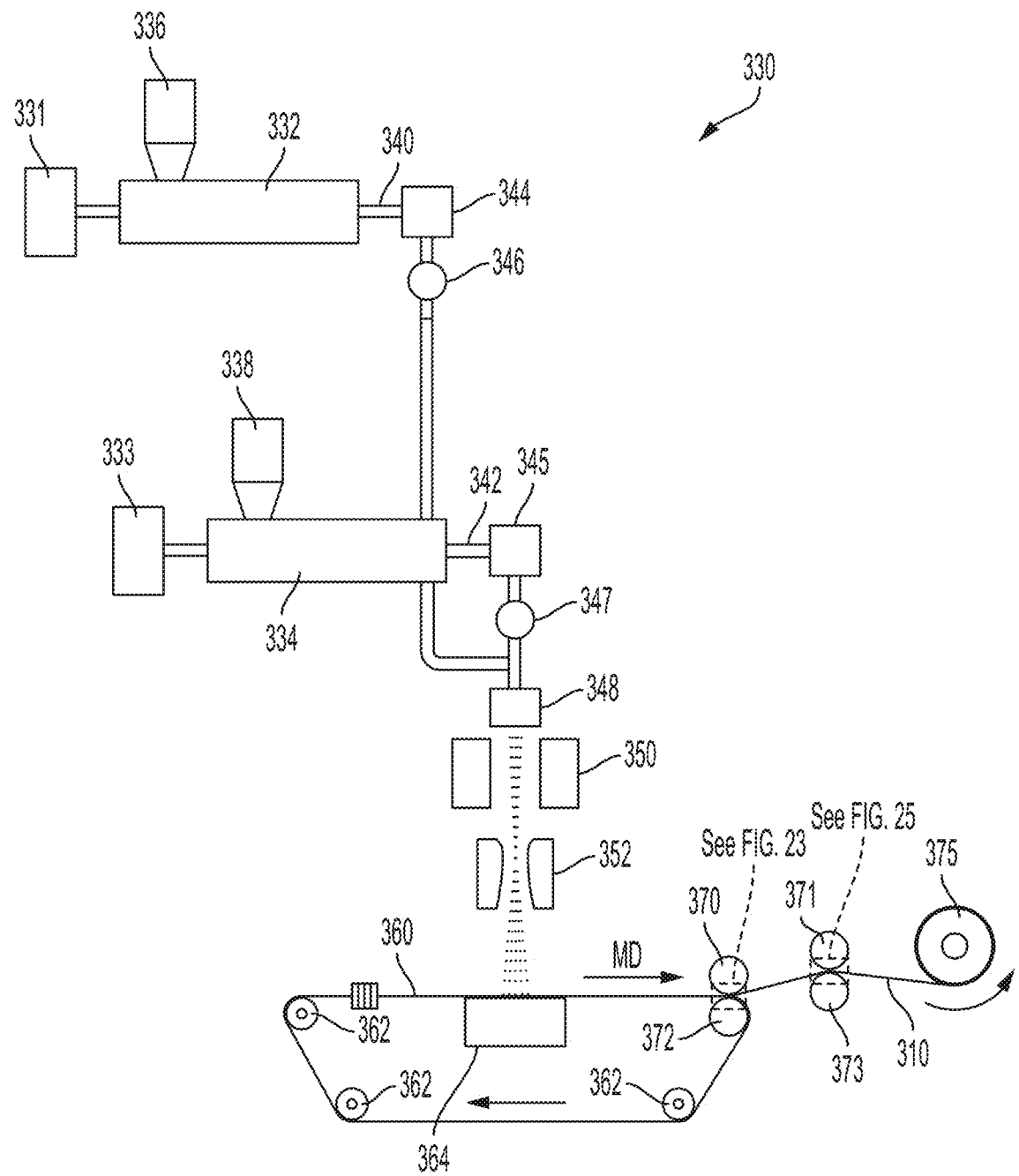
FIG. 22 is a schematic representation of an example apparatus for making the nonwoven webs of the present disclosure.

Referring to FIG. 22, a representative process line 330 for manufacturing some example nonwoven webs made on a structured forming belt of the present disclosure is illustrated. The process line 330 is arranged to produce a nonwoven web of bicomponent continuous filaments, but it should be understood that the present disclosure comprehends nonwoven webs made with monocomponent or multicomponent filaments having more than two components. The bicomponent filaments may or may not be trilobal.

The process line 330 may comprise a pair of extruders 332 and 334 driven by extruder drives 331 and 333, respectively, for separately extruding the primary polymer component A and the secondary polymer component B. Polymer component A may be fed into the respective extruder 332 from a first hopper 336 and polymer component B may be fed into the respective extruder 334 from a second hopper 338. Polymer components A and B may be fed from the extruders 332 and 334 through respective polymer conduits 340 and 342 to filters 344 and 345 and melt pumps 346 and 347, which pump the polymer into a spin pack 348. Spinnerets for extruding bicomponent filaments are generally known to those of ordinary skill in the art.

Generally described, the spin pack 348 comprises a housing which comprises a plurality of plates stacked one on top of the other with a pattern of openings arranged to create flow paths for directing polymer components A and B separately through the spinneret. The spin pack 348 has openings arranged in one or more rows. The spinneret openings form a downwardly extending curtain of filaments when the polymers are extruded through the spinneret. For the purposes of the present disclosure, spinnerets may be arranged to form side-by-side, eccentric sheath/core, or sheath/core bicomponent filaments as illustrated in FIGS. 20A-20C, as well as non-round fibers, such as tri-lobal fibers as shown in FIG. 21. Moreover, the fibers may be monocomponent having one polymeric component, such as polypropylene, for example.

The process line 330 may comprises a quench blower 350 positioned adjacent to the curtain of filaments extending from the spinneret. Air from the quench air blower 350 may quench the filaments extending from the spinneret. The quench air may be directed from one side of the filament curtain or both sides of the filament curtain.

An attenuator 352 may be positioned below the spinneret and receives the quenched filaments. Fiber draw units or aspirators for use as attenuators in melt spinning polymers are generally known to those of skill in the art. Suitable fiber draw units for use in the process of forming the nonwoven webs of the present disclosure may comprise a linear fiber attenuator of the type shown in U.S. Pat. No. 3,802,817 and eductive guns of the type shown in U.S. Pat. Nos. 3,692,618 and 3,423,266.

Generally described, the attenuator 352 may comprise an elongate vertical passage through which the filaments are drawn by aspirating air entering from the sides of the passage and flowing downwardly through the passage. A structured, endless, at least partially foraminous, forming belt 360 may be positioned below the attenuator 352 and may receive the continuous filaments from the outlet opening of the attenuator 352. The forming belt 360 may travel around guide rollers 362. A vacuum 364 positioned below the structured forming belt 360 where the filaments are deposited draws the filaments against the forming surface. Although the forming belt 360 is shown as a belt in FIG. 22, it should be understood that the forming belt may also be in other forms such as a drum. Details of particular shaped forming belts are explained below.

In operation of the process line 330, the hoppers 336 and 338 are filled with the respective polymer components A and B. Polymer components A and B are melted and extruded by the respective extruders 332 and 334 through polymer conduits 340 and 342 and the spin pack 348. Although the temperatures of the molten polymers vary depending on the polymers used, when polyethylenes are used as primary component A and secondary component B respectively, the temperatures of the polymers may range from about 190° C. to about 240° C., for example.

As the extruded filaments extend below the spinneret, a stream of air from the quench blower 350 at least partially quench the filaments, and, for certain filaments, to induce crystallization of molten filaments. The quench air may flow in a direction substantially perpendicular to the length of the filaments at a temperature of about 0° C. to about 35° C. and a velocity from about 100 to about 400 feet per minute. The filaments may be quenched sufficiently before being collected on the forming belt 360 so that the filaments may be arranged by the forced air passing through the filaments and the forming belt 360. Quenching the filaments reduces the tackiness of the filaments so that the filaments do not adhere to one another too tightly before being bonded and may be moved or arranged on the forming belt 360 during collection of the filaments on the forming belt 360 and formation of the nonwoven web.

After quenching, the filaments are drawn into the vertical passage of the attenuator 352 by a flow of the fiber draw unit. The attenuator may be positioned 30 to 60 inches below the bottom of the spinneret.

The filaments may be deposited through the outlet opening of the attenuator 352 onto the shaped, traveling forming belt 360, As the filaments are contacting the forming surface of the forming belt 360, the vacuum 364 draws the air and filaments against the forming belt 360 to form a nonwoven web of continuous filaments which assumes a shape corresponding to the shape of the structured forming surface of the structured forming belt 360. As discussed above, because the filaments are quenched, the filaments are not too tacky and the vacuum may move or arrange the filaments on the forming belt 360 as the filaments are being collected on the forming belt 330 and formed into nonwoven webs.

The process line 330 may comprise one or more bonding devices such as the cylinder-shaped compaction rolls 370 and 372, which form a nip through which the nonwoven web may be compacted (e.g., calendared) and which may be heated to bond fibers as well. One or both of compaction rolls 370, 372 may be heated to provide enhanced properties and benefits to the nonwoven webs by bonding portions of the nonwoven webs. For example, it is believed that heating sufficient to provide thermal bonding improves the nonwoven web's tensile properties. The compaction rolls may be pair of smooth surface stainless steel rolls with independent heating controllers. The compaction rolls may be heated by electric elements or hot oil circulation. The gap between the compaction rolls may be hydraulically controlled to impose desired pressure on the nonwoven web as it passes through the compaction rolls on the forming belt. As an example, with a forming belt caliper of 1.4 mm, and a spunbond nonwoven web having a basis weight of 25 gsm, the nip gap between the compaction rolls 370 and 372 may be about 1.4 mm.

Figure 23:
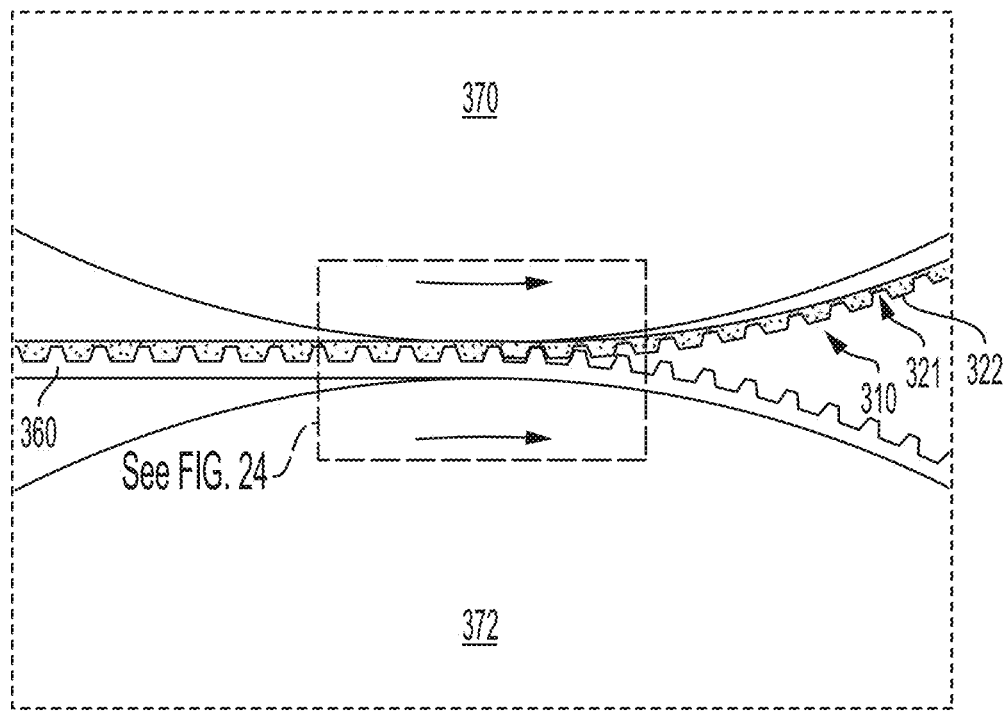
FIG. 23 is a detail of a portion of the apparatus of FIG. 22 for bonding a portion of the nonwoven webs of the present disclosure.
Figure 24:
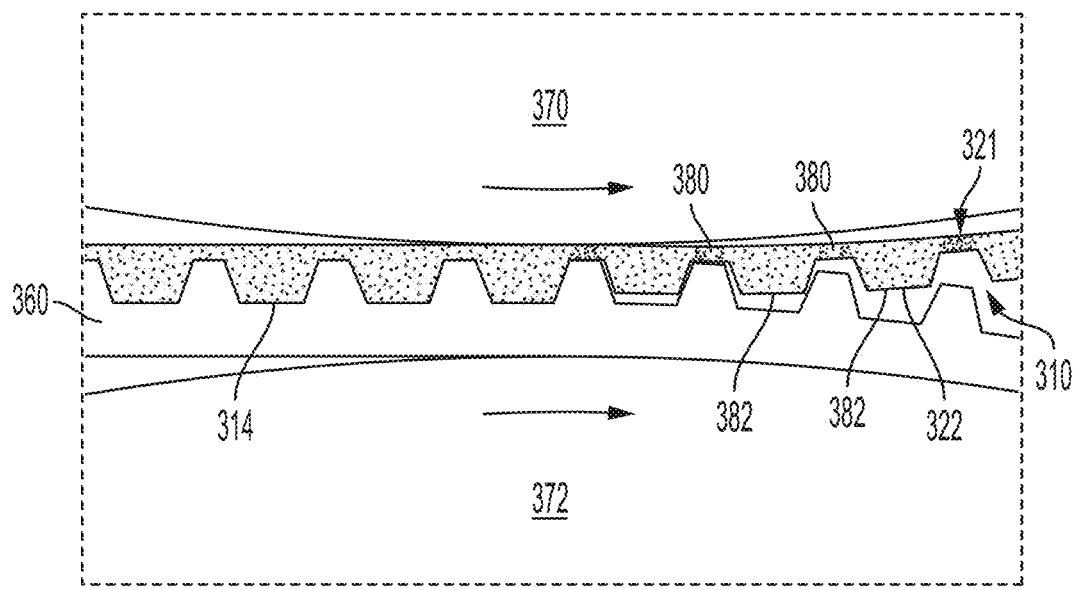
FIG. 24 is a further detail of a portion of the apparatus for bonding a portion of the nonwoven webs of the present disclosure, taken from detail FIG. 2.4 in FIG. 23.

An upper compaction roll 370 may be heated sufficiently to consolidate or melt fibers on a first surface of a nonwoven web 310, to impart strength to the nonwoven web so that it may be removed from forming belt 360 without losing integrity. As shown in FIGS. 23 and 24, for example, as rolls 370 and 372 rotate in the direction indicated by the arrows, the forming belt 360 with the spunbond web laid down on it enter the nip formed by rolls 370 and 372. Heated roll 370 may heat, the portions of the nonwoven web 310 that are pressed against it by the raised resin elements of belt 360, i.e., in regions 321, to create bonded fibers 380 on at least the first surface of the nonwoven web 310. As can be understood by the description herein, the bonded regions so formed may take the pattern of the raised elements of forming belt 360. By adjusting temperature and dwell time, the bonding may be limited primarily to fibers closest to the first surface of the nonwoven web 310, or thermal bonding may be achieved to a second surface. Bonding may also be a discontinuous network, for example, as point bonds 390, discussed below.

The raised elements of the forming belt 360 may be selected to establish various network characteristics of the forming belt and the bonded regions of the nonwoven web 310. The network corresponds to resin making up the raised elements of the forming belt 360 and may comprise substantially continuous, substantially semi-continuous, discontinuous, or combinations thereof options. These networks may be descriptive of the raised elements of the forming belt 360 as it pertains to their appearance or make-up in the X-Y planes of the forming belt 360 or the three-dimensional features of the nonwoven webs 310.

Figure 25:
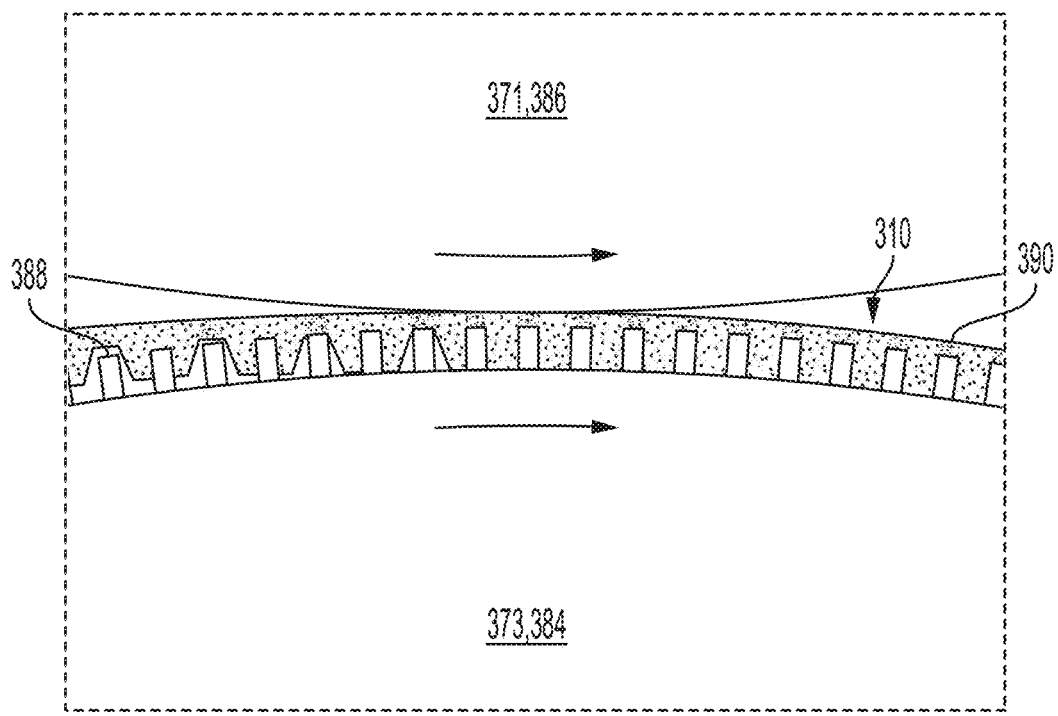
FIG. 25 is a detail of a portion of the apparatus for optional additional bonding of a portion of the nonwoven webs of the present disclosure.
Figure 26:
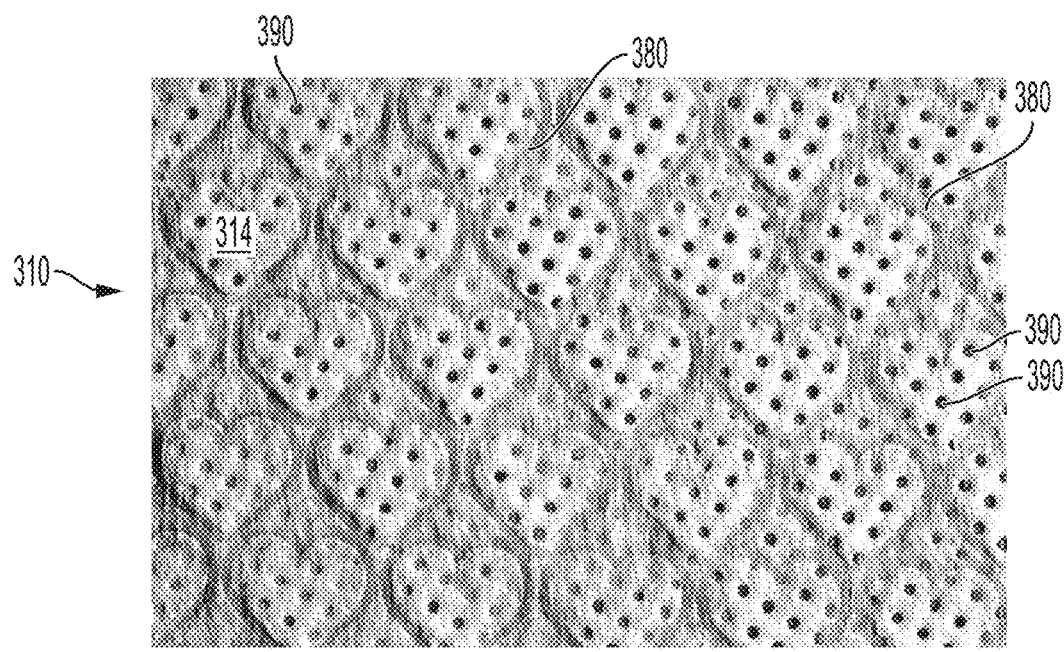
FIG. 26 is a photograph of an example nonwoven web with a different design than the nonwoven webs of the present disclosure.

After compaction, the nonwoven web 310 may leave the forming belt 360 and be calendared through a nip formed by calendar rolls 371, 373, after which the nonwoven web 310 may be wound onto a reel 375 or conveyed directly into a manufacturing operation for products, such as absorbent articles. As shown in the schematic cross-section of FIG. 25, the calendar rolls 371, 373 may be stainless steel rolls having an engraved pattern roll 384 and a smooth roll 386. The engraved roll may have raised portions 388 that may provide for additional compaction and bonding to the nonwoven web 310. Raised portions 388 may be a regular pattern of relatively small spaced apart "pins" that form a pattern of relatively small point bonds 390 in the nip of calendar rolls 371 and 373. The percent of point bonds in the nonwoven web 10 may be from about 3% to about 30% or from about 7% to about 20%, for example. The engraved pattern may be a plurality of closely spaced, regular, generally cylindrically-shaped, generally flat-topped pin shapes, with pin heights being in a range of about 0.5 mm to about 5 mm or from about 1 mm to about 3 mm, for example. Pin bonding calendar rolls may form closely spaced, regular point bonds 390 in the nonwoven web 10, as shown in an example in FIG. 26. Further bonding may be by hot-air-through bonding, for example. FIG. 26 shows a hearts pattern made by the same structured forming belt technology that may be used to make the nonwoven webs of the present disclosure. FIG. 26 is only an example of a pattern, although the visually discernable patterns comprising the three-dimensional features shown, for example, in FIGS. 13-19, are more applicable to the present disclosure.

"Point bonding", as used herein, is a method of thermally bonding a nonwoven web. This method comprises passing a web through a nip between two rolls comprising a heated male patterned or engraved metal roll and a smooth or patterned metal roll. The male patterned roll may have a plurality of raised, generally cylindrical-shaped pins that produce circular point bonds. The smooth roll may or may not be heated, depending on the application. In a nonwoven manufacturing line, the nonwoven web, which could be a non-bonded nonwoven web, is fed into the calendar nip and the fiber temperature is raised to the point for fibers to thermally fuse with each other at the tips of engraved points and against the smooth roll. The heating time is typically in the order of milliseconds. The nonwoven web properties are dependent on process settings such as roll temperatures, web line speeds, and nip pressures, all of which may be determined by the skilled person for the desired level of point bonding. Other types of point bonding known generally as hot calendar bonding may use different geometries for the bonds (other than circular shaped), such as oval, lines, circles, for example. In an example, the point bonding produces a pattern of point bonds being 0.5 mm diameter circles with 10% overall bonding area. Other bonding shapes may have raised pins having a longest dimension across the bonding surface of a pin of from about 0.1 mm to 2.0 mm and the overall bonding area ranges from about 5% to about 30%, for example.

As shown in FIG. 26, a heated compaction roll 370 may form a bond pattern, which may be a substantially continuous network bond pattern 380 (e.g., interconnected heart shaped bonds) on a first surface of the nonwoven web 310 (not shown in FIG. 26, as it faces away from the viewer), and the engraved calendar roll 373 may form relatively small point bonds 390 on a second surface 314 of the nonwoven web. The point bonds 390 may secure loose fibers that would otherwise be prone to fuzzing or pilling during use of the nonwoven web 310. The advantage of the resulting structure of the nonwoven web 310 is most evident when used as a topsheet or outer cover nonwoven material in an absorbent article, such as a diaper, for example. In use, in an absorbent article, a first surface of the nonwoven web 310 may be relatively flat (relative to second surface 14) and have a relatively large amount of bonding due to the heated compaction roll forming bonds 380 at the areas of the nonwoven web pressed by the raised elements of the forming belt 360. This bonding gives the nonwoven web 310 structural integrity, but still may be relatively stiff or rough to the skin of a user. Therefore, a first surface of the nonwoven web 310 may be oriented in a diaper or sanitary napkin to face the interior of the article, i.e., away from the body of the wearer or garment-facing. Likewise, the second surface 314 may be wearer-facing in use, and in contact with the body. The relatively small point bonds 390 may be less likely to be perceived visually or tacitly by the user, and the relatively soft three-dimensional features may remain visually free of fuzzing and pilling while feeling soft to the body in use. Further bonding may be used instead of, or in addition to, the above-mentioned bonding. Through-air bonding may also be used.

The forming belt 360 may be made according to the methods and processes described in U.S. Pat. No. 6,610,173, issued to Lindsay et al., on Aug. 26, 2003, or U.S. Pat. No. 5,514,523, issued to Trokhan et al., on May 7, 1996, or U.S. Pat. No. 6,398,910, issued to Burazin et al., on Jun. 4, 2002, or U.S. Pat. No. 8,940,376, issued to Stage et al., on Jan. 27, 2015, each with the improved features and patterns disclosed herein for making spunbond nonwoven webs. The Lindsay, Trokhan, Burazin, and Stage disclosures describe structured forming belts that are representative of papermaking belts made with cured resin on a woven reinforcing member, which belts, with improvements, may be utilized to form the nonwoven webs of the present disclosure as described herein.

Figure 27:
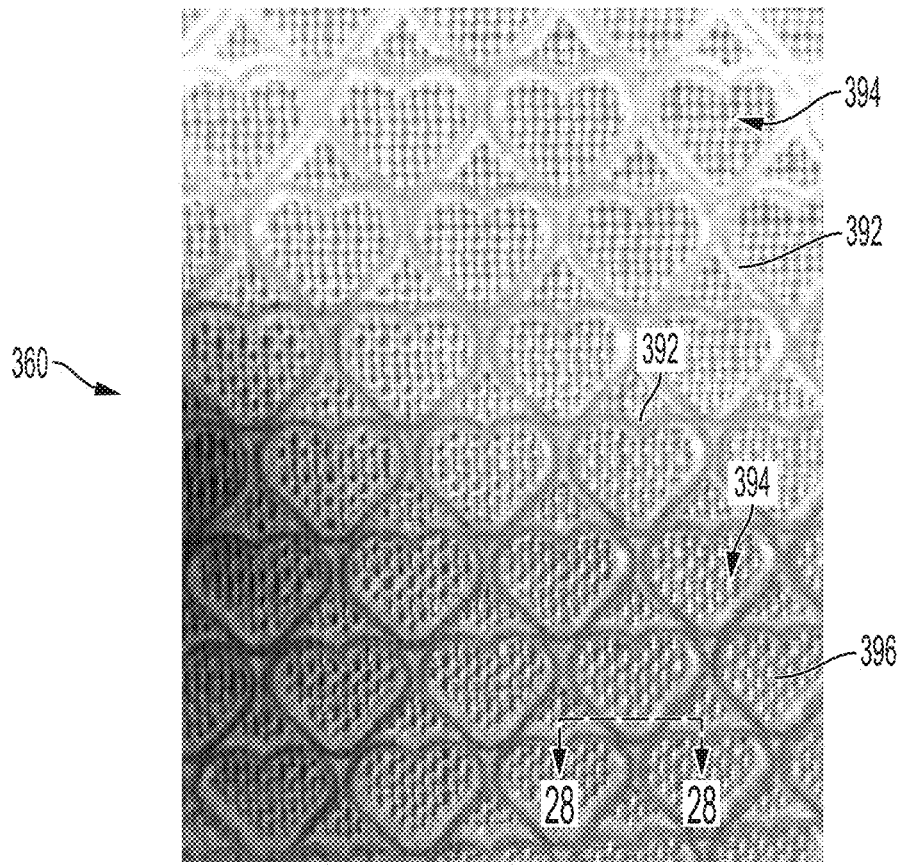
FIG. 27 is a photograph of a portion of a forming belt with the different design for forming nonwoven webs.

An example of a structured forming belt 360, and which may be made according to the disclosure of U.S. Pat. No. 5,514,523, is shown in FIG. 27. As taught therein, a reinforcing member 394 (such as a woven belt of filaments 396) is thoroughly coated with a liquid photosensitive polymeric resin to a preselected thickness. A film or negative mask incorporating the desired raised element pattern repeating elements (e.g., FIG. 29) is juxtaposed on the liquid photosensitive resin. The resin is then exposed to light of an appropriate wave length through the film, such as UV light for a UV-curable resin. This exposure to light causes curing of the resin in the exposed areas (i.e., white portions or non-printed portions in the mask). Uncured resin (resin under the opaque portions in the mask) is removed from the system leaving behind the cured resin forming the pattern illustrated, for example, the cured resin elements 392 shown in FIG. 27, Other patterns may also be formed, such as the patterns illustrated in FIGS. 13 to 19.

Figure 28:
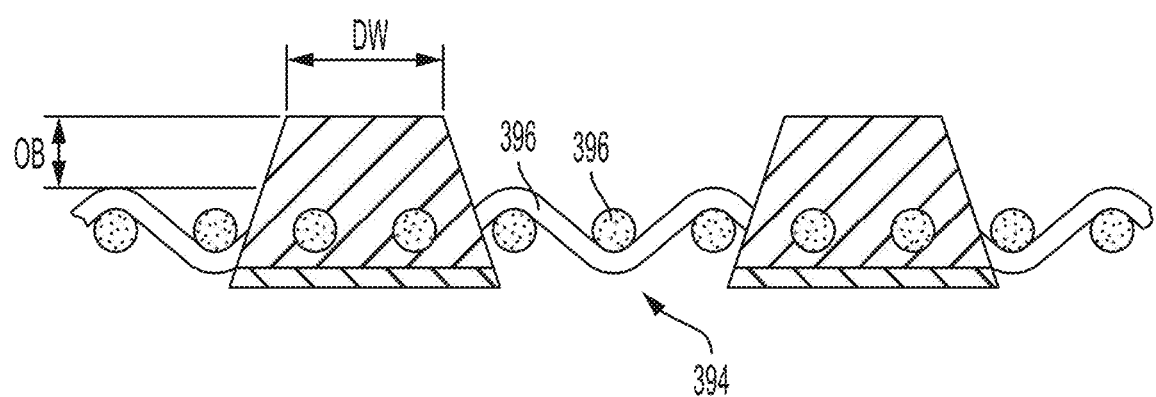
FIG. 28 is a cross-sectional depiction of a portion of the forming belt, taken about line 28-28 of FIG. 27.
Figure 29:
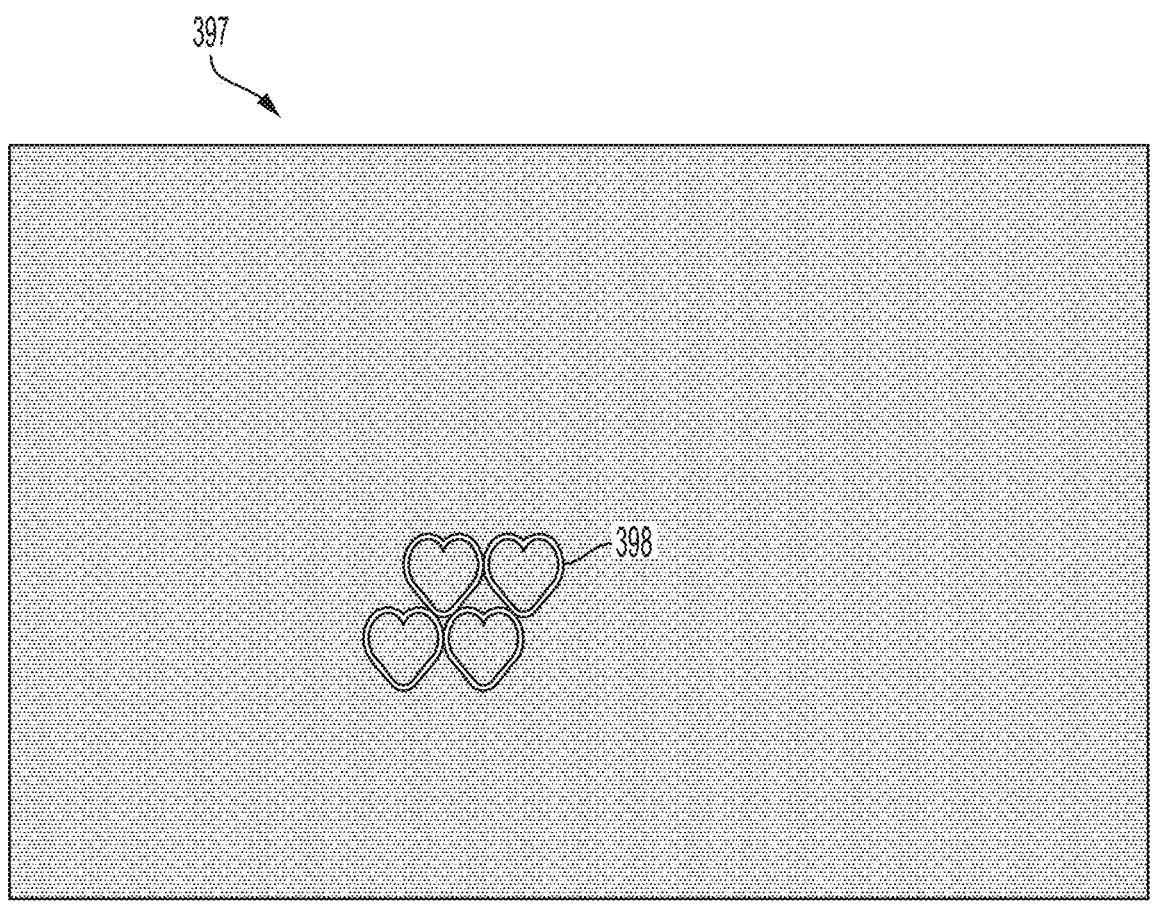
FIG. 29 is an image of a portion of a mask utilized to at least in part create the forming belt of FIG. 27.

The forming belt 360 may comprise cured resin elements 392 on a woven reinforcing member 394. The reinforcing member 394 may be made of woven filaments 396 as is generally known in the art of papermaking belts, including resin coated papermaking belts. The cured resin elements may have the general structure depicted in FIG. 27, and are made by the use of a mask 397 having the dimensions indicated in FIG. 329 As shown in schematic cross-section in FIG. 28, cured resin elements 392 flow around and are cured to "lock on" to the reinforcing member 394 and may have a width at a distal end DW of about 0.020 inches to about 0.060 inches, or from about 0.025 inches to about 0.030 inches, and a total height above the reinforcing member 394, referred to as over burden, OB, of about 0.030 inches to about 0.120 inches or about 0.50 inches to about 0.80 inches, or about 0.040 inches. FIG. 29 represents a portion of a mask 397 showing the design and representative dimensions for one repeat unit of the repeating hearts design, shown herein merely as an example. The white portion 398 is transparent to UV light, and in the process of making the belt, as described in U.S. Pat. No. 5,514,523, permits UV light to cure an underlying layer of resin which is cured to form the raised elements 392 on the reinforcing member 394. After the uncured resin is washed away, the forming belt 360 having a cured resin design as shown in FIG. 27 is produced by seaming the ends of a length of the forming belt, the length of which may be determined by the design of the apparatus, as depicted in FIG. 22.

Figure 30:
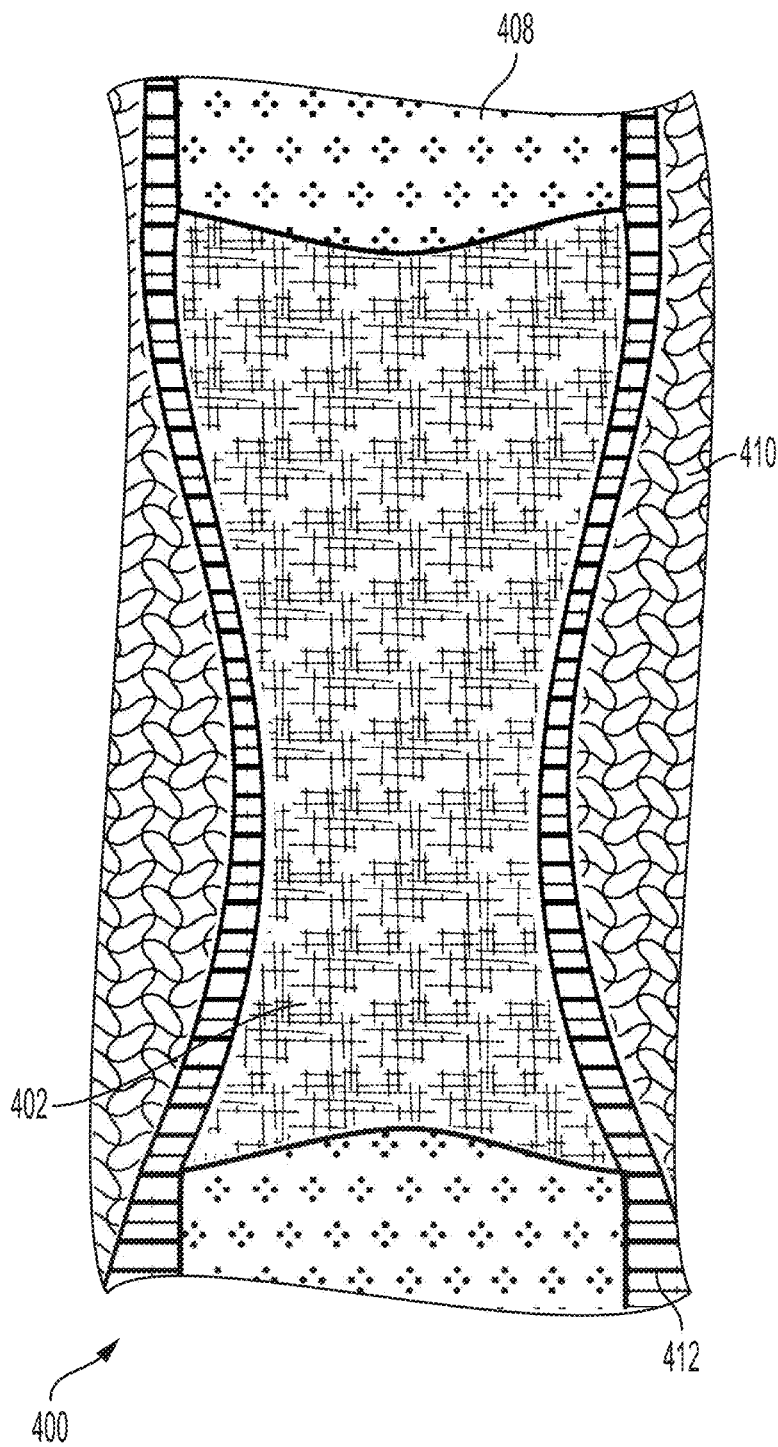
FIG. 30 is an example of a mask 400 for producing a structured forming belt.
Figure 31:
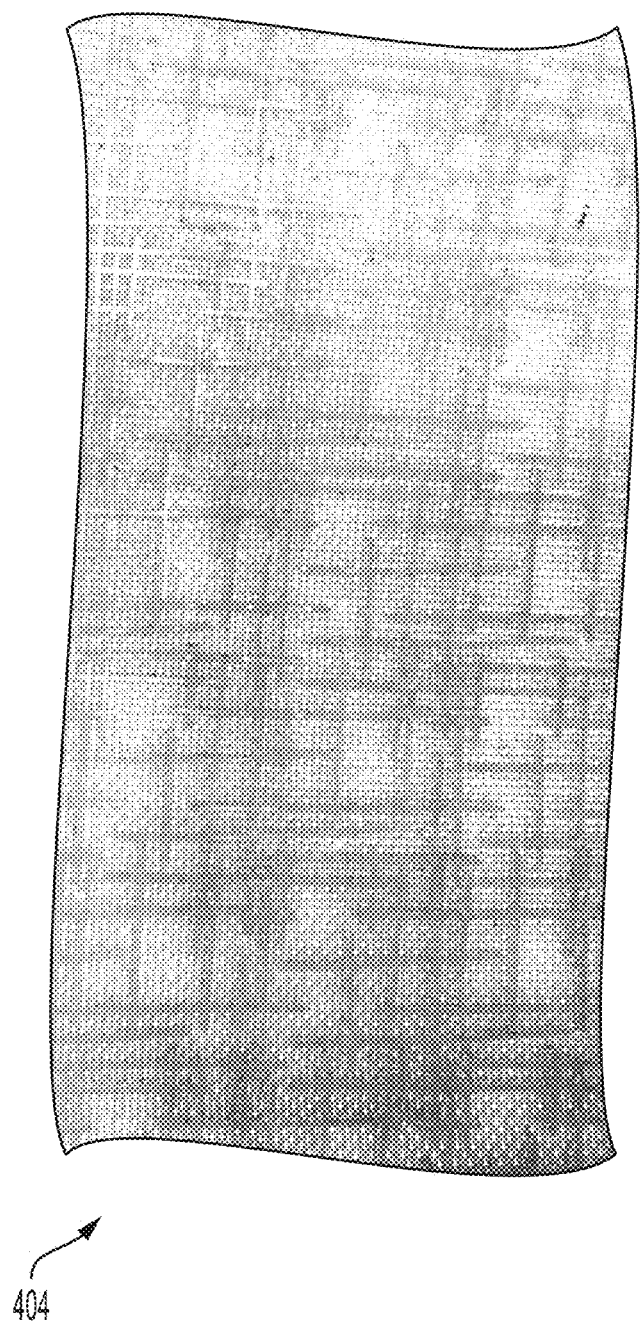
FIG. 31 is an example of a portion of a structured forming belt for producing the nonwoven webs of the present disclosure.
Figure 32:
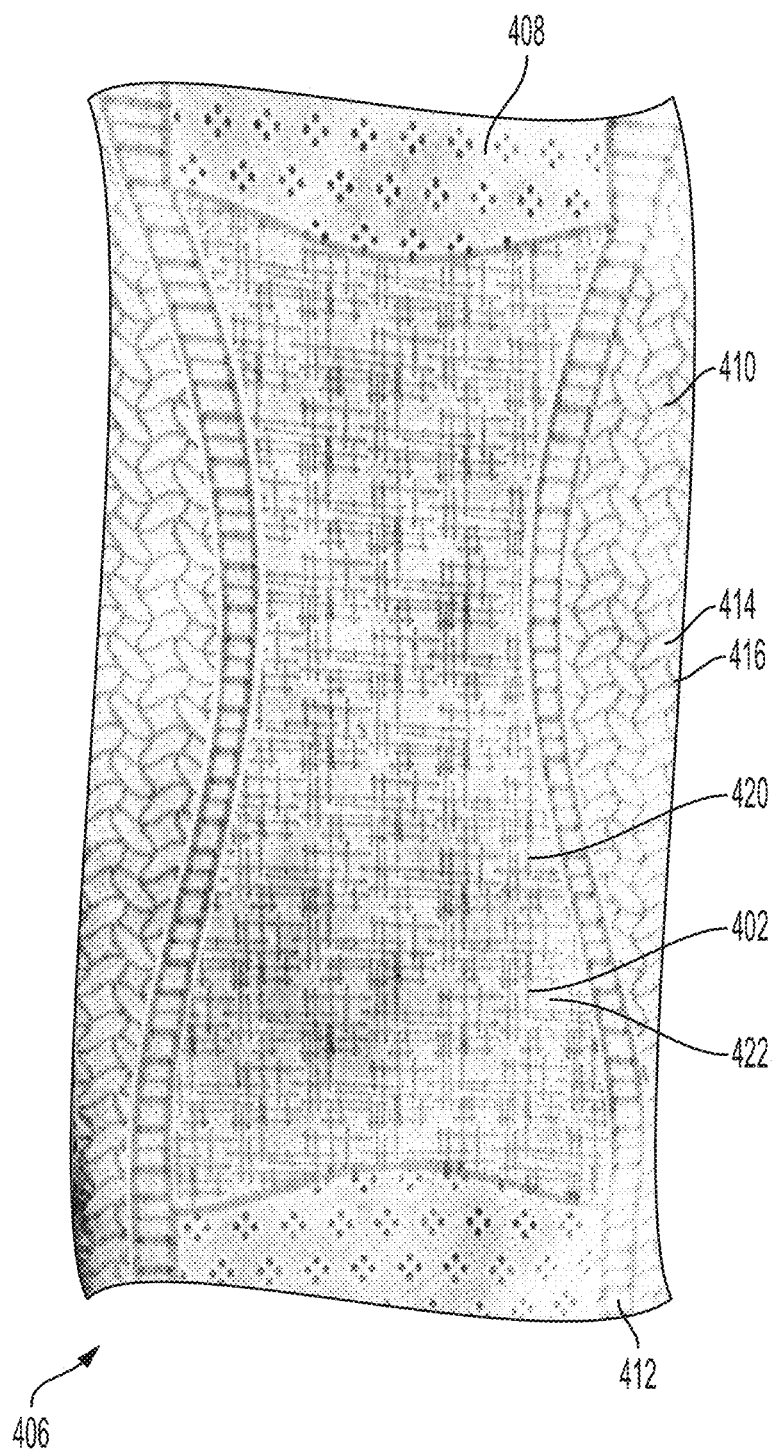
FIG. 32 is an example nonwoven web of the present disclosure, wherein a central portion has the visually discernible pattern shown generally in FIGS. 13-19.

Now that the generally process and forming belt have been described, examples of masks and forming belts of the nonwoven webs comprising visually discernable patterns of three-dimensional elements are disclosed in FIGS. 30-32. FIG. 30 is an example of a mask 400 for producing a structured forming belt. The central portion 402 of the mask 400 illustrates the visually discernable patterns shown generally in FIGS. 13-19. FIG. 31 is an example of a portion of a structured forming belt 404 for producing the nonwoven webs of the present disclosure. FIG. 32 is an example nonwoven web 406 of the present disclosure, where the central portion 402 has the visually discernible pattern shown generally in FIGS. 13-19.

Referring to FIG. 30, the white portions of the mask 400 will form raised areas of resin on the structured forming belt 404, while the black portions will not be cured and will be washed away from the structured forming belt 404. In another form, the white and black portions could be reversed, and the visually discernible pattern would be formed where cured resin is not present on the belt. FIG. 31 illustrates the portion of structured forming belt pattern 404 of the central portion 402 of the mask 400. In this instance, the raised portions have resin, while the other portions do not.

The nonwoven webs comprising the visually discernible patterns of three-dimensional elements of the present disclosure may also have other visually discernible patterns of three-dimensional features 408, 410, 412, as shown in FIGS. 30 and 32. While the other patterns may be embossed or hydroentangled, they may also be formed using the structured forming belts described herein and process thereof. The other (or second, third, and fourth) visually discernible patterns of three-dimensional features 408, 410, and 412 may each comprise a microzone comprising a first region 414 and a second region 416 (visually discernible pattern 410 is used an example). The first region 414 may be formed where black is present on the mask 400 and the second region 416 may be formed where white is present on the mask 400. As such, the first region 414 may be less densified than the second region 416. The first region 414 may have an average intensive property having a first value and the second region 416 may have the average intensive property having a second value. The first value may be different than the second value. The average intensive property may be caliper, basis weight, or volumetric density. The other visually discernible patterns of three-dimensional features may include a different pattern of FIGS. 13-19 vs. completely different pattern as shown in FIG. 32.

Referring now to the central portion 402 of the nonwoven web 406 of FIG. 32, the visually discernible pattern of three-dimensional features may comprise first regions 420 (substantially linear segments) and second regions 422 (regions surrounding the substantially linear elements). The first regions 420 may have an average intensive property having a first value and the second regions 422 may have the average intensive property having a second value. The first and second values may be different. The average intensive property may be caliper, basis weight, or volumetric density.

The nonwoven webs disclosed herein may be fluid permeable. The entire nonwoven web may be considered fluid permeable or some regions may be fluid permeable. By fluid permeable, as used herein, with respect to the nonwoven web is meant that the nonwoven web has at least one region which permits liquid to pass through under in-use conditions of a consumer product or absorbent article. For example, if used as a topsheet on a disposable absorbent article, the nonwoven web may have at least one zone having a level of fluid permeability permitting urine to pass through to an underlying absorbent core. By fluid permeable as used herein with respect to a region is meant that the region exhibits a porous structure that permits liquid to pass through.

Referring again to FIG. 32, an example nonwoven web of the present disclosure is illustrated. The nonwoven web has a plurality of visually discernible patterns of three-dimensional elements comprising first regions 414 and second regions 416. The first and second regions of each of the patterns 420, 408, 410, 412 are recognizably different visually. A visually discernible difference exists if an observer in ordinary indoor lighting conditions (20/20 vision, lighting sufficient to read by, for example) may visually discern a pattern difference between the zones, such as the first region 414 and the second region 416 of pattern 410.

Because of the nature of the structured forming belts and other apparatus elements, as described herein, the three-dimensional features of the nonwoven web have average intensive properties that may differ between first and second regions, or from feature to feature in ways that provide for beneficial properties of the nonwoven web when used in personal care articles, garments, medical products, and cleaning products. For example, a first region may have a basis weight or density that is different from the basis weight or density of a second region, and both may have a basis weight or density that is different from that of a third region, providing for beneficial aesthetic and functional properties related to fluid acquisition, distribution and/or absorption in diapers or sanitary napkins.

The average intensive property differential between the various regions of the nonwoven webs is believed to be due to the fiber distribution and compaction resulting from the apparatus and method described herein. The fiber distribution occurs during the fiber laydown process, as opposed to, for example, a post making process such as embossing processes. Because the fibers are free to move during a process such as a melt spinning process, with the movement determined by the nature of the features and air permeability of the forming belt and other processing parameters, the fibers are believed to be more stable and permanently formed in nonwoven web.

In structured forming belts having multiple zones, the air permeability in each zone may be variable such that the intensive properties of average basis weight and average volumetric density in the zones may be varied. Variable air permeabilities in the various zones causes fiber movement during laydown. The air permeability may be between about 400 to about 1000 cfm, or between about 400 to about 800 cfm, or between about 500 cfm and about 750 cfm, or between about 650 to about 700 cfm, specifically reciting all 1 cfm increments within the specified ranges and all ranges formed therein or thereby.

Examples Combinations:
1. A nonwoven web for an absorbent article, the nonwoven web comprising:
   a first surface;
   a second surface; and
   a repeat unit comprising:
      a visually discernible pattern of three-dimensional features on the first surface or the second surface, wherein the three-dimensional features comprise one or more first regions and a plurality of second regions, and wherein the plurality of second regions comprise 10 to 100 irregular varying regions, according to the Pattern Analysis Test.
2. The nonwoven web for an absorbent article of Paragraph 1, wherein the one or more first regions comprise a plurality of substantially linear segments.
3. The nonwoven web for an absorbent article of Paragraph 1 or 2, wherein the plurality of second regions comprising the 10 to 100 irregular varying regions have an Area Variability of greater than 50%, but less than 150%, according to the Pattern Analysis Test.
4. The nonwoven web for an absorbent article of any one of the preceding Paragraphs, wherein the plurality of second regions comprising the 10 to 100 irregular varying regions have a Shape Variability of greater than 20%, but less than 120%, according to the Pattern Analysis Test.
5. The nonwoven web for an absorbent article of any one of the preceding Paragraphs, wherein at least some of the 10 to 100 irregular varying regions comprise a peninsular shape.
6. The nonwoven web for an absorbent article of any one of the preceding Paragraphs, wherein the plurality of second regions comprising the 10 to 100 irregular varying regions are free of the plurality of substantially linear segments.
7. The nonwoven web for an absorbent article of any one of the preceding Paragraphs, wherein the one or more first regions have an average intensive property having a first value, and wherein the plurality of second regions comprising the 10 to 100 irregular varying regions have the average intensive property having a second, different value.
8. The nonwoven web for an absorbent article of Paragraph 7, wherein the average intensive property is caliper, basis weight, or volumetric density.
9. The nonwoven web for an absorbent article of Paragraph 2, wherein the plurality of substantially linear segments comprise a first group of the plurality of substantially linear segments and a second group of the plurality of substantially linear segments, wherein the first group of the plurality of substantially linear segments intersects with the second group of the plurality of substantially linear segments at angles of intersection, and wherein the angles of intersection are in the range of about 70 degrees to about 110 degrees.
10. The nonwoven web for an absorbent article of any one of Paragraphs 1-6 and 9, wherein the visually discernable pattern is embossed.
11. The nonwoven web for any absorbent article of any one of Paragraphs 1-6 and 9, wherein the visually discernable pattern is hydroentangled.
12. The nonwoven web for an absorbent article of any one of the preceding Paragraphs, comprising a second visually discernible pattern of three-dimensional elements on the first surface or the second surface and outside of the repeat unit, wherein each of the three-dimensional elements define a microzone comprising a first region and a second region.
13. The nonwoven web for an absorbent article of any one of Paragraphs 1-11, comprising a second visually discernible pattern of three-dimensional elements on the first surface or the second surface and outside of the repeat unit, wherein the three-dimensional elements comprise one or more third regions and a plurality of fourth regions, and wherein the one or more third regions comprise a plurality of substantially linear segments.
14. The nonwoven web for an absorbent article of any one of the preceding Paragraphs, wherein the nonwoven web is formed on a structured forming belt.
15. An absorbent article comprising the nonwoven web of any one of the preceding Paragraphs.
16. The absorbent article of Paragraph 15, comprising:
   a liquid permeable topsheet;

a liquid permeable backsheet; and an absorbent core positioned at least partially intermediate the topsheet and the backsheet.

17. The absorbent article of Paragraph 16, wherein the topsheet comprises the nonwoven web.

18. The absorbent article of Paragraph 16, comprising an outer cover nonwoven material in a facing relationship with the backsheet, wherein the nonwoven web comprises the outer cover nonwoven material.

19. A nonwoven web for an absorbent article, the nonwoven web comprising:
- a first surface;
- a second surface; and
- a repeat unit comprising:
  - a visually discernible pattern of three-dimensional features on the first surface or the second surface, wherein the three-dimensional features comprise one or more first regions and a plurality of second regions, and wherein the plurality of second regions have an Area Variability of greater than 50%, but less than 150%, according to the Pattern Analysis Test.

20. The nonwoven web for an absorbent article of Paragraph 19, wherein the plurality of second regions comprise 10 to 100 irregular varying regions, according to the Pattern Analysis Test.

21. The nonwoven web for an absorbent article of Paragraph 19 or 20, wherein the plurality of second regions have a Shape Variability of greater than 20%, but less than 120%, according to the Pattern Analysis Test.

22. The nonwoven web for an absorbent article of any one of Paragraphs 19-21, wherein at least some of the plurality of second regions comprise a peninsular shape.

23. A nonwoven web for an absorbent article, the nonwoven web comprising:
- a first surface;
- a second surface; and
- a repeat unit comprising:
  - a visually discernible pattern of three-dimensional features on the first surface or the second surface, wherein the three-dimensional features comprise one or more first regions and a plurality of second regions, and wherein the plurality of second regions have a Shape Variability of greater than 20%, but less than 120%, according to the Pattern Analysis Test.

24. The nonwoven web for an absorbent article of Paragraph 23, wherein the plurality of second regions comprise 10 to 100 irregular varying regions, according to the Pattern Analysis Test.

25. The nonwoven web for an absorbent article of any one of Paragraphs 23 or 24, wherein the plurality of second regions have an Area Variability of greater than 50%, but less than 150%, according to the Pattern Analysis Test.

26. The nonwoven web for an absorbent article of any one of Paragraphs 23-25, wherein at least some of the plurality of second regions comprise a peninsular shape.

27. A nonwoven web for an absorbent article, the nonwoven web comprising:
- a first surface;
- a second surface; and
- a repeat unit comprising:
  - a visually discernible pattern of three-dimensional features on the first surface or the second surface, wherein the three-dimensional features comprise one or more first regions and a plurality of second regions, and wherein at least some of the plurality of second regions comprise a peninsular shape.

28. The nonwoven web for an absorbent article of Paragraph 27, wherein the plurality of second regions have a Shape Variability of greater than 20%, but less than 120%, according to the Pattern Analysis Test.

29. The nonwoven web for an absorbent article of Paragraph 27 or 28, wherein the plurality of second regions comprise 10 to 100 irregular varying regions, according to the Pattern Analysis Test.

30. The nonwoven web for an absorbent article any one of Paragraphs 27-29, wherein the plurality of second regions have an Area Variability of greater than 50%, but less than 150%, according to the Pattern Analysis Test.

31. A structured forming belt comprising:
- an endless foraminous member comprising a first surface and a second surface; and
- a curable resin extending from the first surface of the foraminous member;
- the resin forming a repeat unit comprising:
  - a visually discernible pattern of three-dimensional features, wherein the three-dimensional features comprise one or more first regions and a plurality of second regions, and wherein the plurality of second regions comprise 10 to 100 irregular varying regions, according to the Pattern Analysis Test.

32. The structured forming belt of Paragraph 31, wherein the one or more first regions comprise a plurality of substantially linear segments that comprise the resin.

33. The structured forming belt of Paragraph 31 or 32, wherein the plurality of second regions comprising the 10 to 100 irregular varying regions have an Area Variability of greater than 50%, but less than 150%, according to the Pattern Analysis Test.

34. The structured forming belt of any one of Paragraphs 31-33, wherein the plurality of second regions comprising the 10 to 100 irregular varying regions have a Shape Variability of greater than 20%, but less than 120%, according to the Pattern Analysis Test.

35. The structured forming belt of any one of Paragraphs 31-34, wherein at least some of the 10 to 100 irregular varying regions comprise a peninsular shape.

36. The structured forming belt of any one of Paragraphs 31-35, wherein the plurality of second regions comprising the 10 to 100 irregular varying regions are free of the plurality of substantially linear segments and the resin.

37. The structured forming belt of any one of Paragraphs 31-36, wherein the plurality of substantially linear segments comprise a first group of the plurality of substantially linear segments and a second group of the plurality of substantially linear segments, wherein the first group of the plurality of substantially linear segments intersects with the second group of the plurality of substantially linear segments at angles of intersection, and wherein the angles of intersection are in the range of about 70 degrees to about 110 degrees.

38. A nonwoven web for an absorbent article, the nonwoven web comprising:
- a first surface;
- a second surface; and
- a repeat unit comprising:
  - a visually discernible pattern of three-dimensional features on the first surface or the second surface, wherein the three-dimensional features comprise one or more first regions and a plurality of second regions, wherein the one or more first regions are different than the plurality of second regions;
  - wherein the plurality of first regions comprise a plurality of substantially linear segments;

wherein a first group of the plurality of substantially linear segments intersects with a second group of the plurality of substantially linear segments at angles of intersection;
wherein the angles of intersection are in the range of about 70 degrees to about 110 degrees;
wherein the first group of the plurality of substantially linear segments comprises a plurality of different lengths; and
wherein the second group of the plurality of substantially linear segments comprises a plurality of different lengths.

39. The nonwoven web for an absorbent article of Paragraph 38, wherein the plurality of second regions are free of the plurality of substantially linear segments.

40. An absorbent article comprising:
   a liquid permeable topsheet;
   a liquid impermeable backsheet;
   an absorbent core positioned at least partially intermediate the topsheet and the backsheet; and
   an outer cover nonwoven material in a facing relationship with the backsheet, the outer cover nonwoven material comprising:
      a surface comprising a repeat unit comprising:
         a visually discernible pattern of three-dimensional features, wherein the three-dimensional features comprise one or more first regions and a plurality of second regions;
         wherein the one or more first regions are different than the plurality of second regions;
         wherein the one or more first regions comprise a plurality of substantially linear segments;
         wherein the plurality of second regions are free of the plurality of substantially linear segments;
         wherein a first group of the plurality of substantially linear segments intersects with a second group of the plurality of substantially linear segments at angles of intersection;
         wherein the angles of intersection are in the range of about 70 degrees to about 110 degrees;
         wherein the first group of the plurality of substantially linear segments comprises a plurality of different lengths; and
         wherein the second group of the plurality of substantially linear segments comprises a plurality of different lengths.

41. The absorbent article of Paragraph 40, wherein one or more first regions comprise a plurality of first regions.

42. A structured forming belt comprising:
   an endless foraminous member comprising a first surface and a second surface; and
   a curable resin extending from the first surface of the foraminous member;
   the resin forming a repeat unit comprising:
      a visually discernible pattern of three-dimensional features, wherein the three-dimensional features comprise one or more first regions and a plurality of second regions, wherein the one or more first regions comprise the resin, and wherein the plurality of second regions are free of the resin;
      wherein the one or more first regions are different than the plurality of second regions;
      wherein the one or more first regions comprise a plurality of substantially linear segments;
      wherein a first group of the plurality of substantially linear segments intersects with a second group of the plurality of substantially linear segments at angles of intersection; and
      wherein the angles of intersection are in the range of about 70 degrees to about 110 degrees.

Test Methods

Air Permeability Test Method

The Air Permeability Test is used to determine the level of air flow in cubic feet per minute (cfm) through a forming belt. The Air Permeability Test is performed on a Texas Instruments model FX3360 Portair Air Permeability Tester, available from Textest AG, Sonnenbergstrasse 72, CFI 8603 Schwerzenbach, Switzerland. The unit utilizes a 20.7 mm orifice plate for air permeability ranges between 300-1000 cfm. If air permeability is lower than 300 cfm the orifice plate needs to be reduced; if higher than 1000 cfm the orifice plate needs to be increased. Air permeability can be measured in localized zones of a forming belt to determine differences in air permeability across a forming belt.

Test Procedure
1. Power on the FX3360 instrument.
2. Select a pre-determined style having the following setup:
   a. Material: Standard
   b. Measurement Property: Air Permeability (AP)
   c. Test Pressure: 125 Pa (pascals)
   d. T-factor: 1.00
   e. Test point pitch: 0.8 inch.
3. Position the 20.7 mm orifice plate on the top side of the forming belt (the side with the three-dimensional protrusions) at the position of interest.
4. Selecting "Spot Measurement" on the touch screen of the testing unit.
5. Reset the sensor prior to measurement, if necessary.
6. Once reset, select the "Start" button to begin measurement.
7. Wait until the measurement stabilizes and record the cfm reading on the screen.
8. Select the "Start" button again to stop measurement.

Basis Weight Test

Basis weight of the nonwoven webs described herein may be determined by several available techniques, but a simple representative technique involves taking an absorbent article or other consumer product, removing any elastic which may be present and stretching the absorbent article or other consumer product to its full length. A punch die having an area of 45.6 cm$^2$ is then used to cut a piece of the nonwoven web (e.g., topsheet, outer cover) from the approximate center of the absorbent article or other consumer product in a location which avoids to the greatest extent possible any adhesive which may be used to fasten the nonwoven web to any other layers which may be present and removing the nonwoven web from other layers (using cryogenic spray, such as Cyto-Freeze, Control Company, Houston, Tex., if needed). The sample is then weighed and dividing by the area of the punch die yields the basis weight of the nonwoven web. Results are reported as a mean of 5 samples to the nearest 0.1 gram per square meter (gsm).

Pattern Analysis Test

Area Variability and Shape Variability are obtained by analysis of a repeat unit within a scaled binary image of a pattern intended to be imparted to a nonwoven web by bonding, embossing, hydroentangling, or by a structured forming belt thereby creating a visually discernible pattern of three-dimensional features comprising one or more first regions, or a plurality of first regions, and a plurality of individual discrete second regions. For the purposes of this method, all patterns and distances are taken to be based on the projection of the bonding, embossing, hydroentangling, or structured forming belt pattern onto a two-dimensional plane.

A test region is identified as the region containing a single distinct repeating pattern. If the test region does not contain a repeat unit, then the entire test region is analyzed as a single repeat unit. A single repeat unit (hereafter "SRU") (for subsequent dimensional measurement) within the test region having the repeating pattern comprising the plurality of repeating units is defined as follows. An arbitrary point within the pattern is identified, referred to hereafter as the "chosen point" (hereafter "CP"). Any other point in the test region recognized to be in an equivalent position based on the translational symmetry of the repeat units is referred to as an "equivalent point" (hereafter "EP"). The SRU is defined as the set of points that are closer (via Euclidean distance) to the center of the CP than to the center of any other EP in the test region. The SRU identified for measurement must not touch the edge of the test region. After finding all points within the SRU, if it is found that the SRU touches the edge of the test region, this procedure is repeated with an alternative CP. The process is repeated until a SRU that does not touch the edge of the test region is identified.

Figure 33:
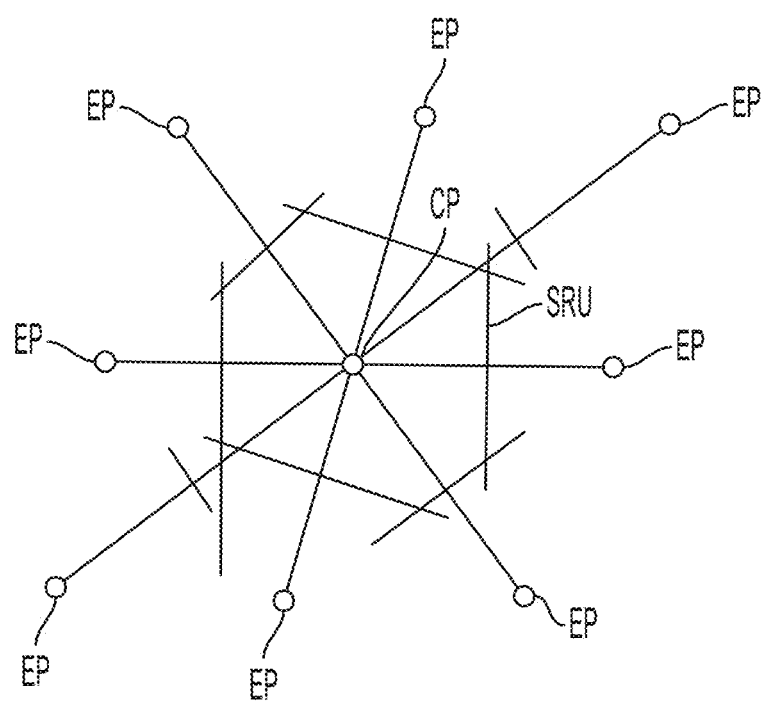
FIG. 33 is an example repeat unit boundary identification linked to the Pattern Analysis Test herein.

One approach to determining the set of points of a SRU is based on identifying a polygonal boundary. Referring to FIG. 33, the boundary of the SRU is the convex polygon formed by the intersection of line segments that immediately border the topsheet region containing the CP. The line segments are identified from lines drawn perpendicular to the midpoint of lines connecting the center of the CP to the center of all neighboring and nearby EP.

Referring to FIG. 17, the SRU length (L) is defined as the feret diameter parallel to the longitudinal axis of the absorbent article, and the SRU width (W) is defined as the feret diameter parallel to the lateral axis of the absorbent article. The feret diameter is the distance between two parallel lines, both of which are tangential to the boundary of the SRU, and is recorded to the nearest 0.1 mm.

The boundaries of the individual discrete second regions bounded by and contained within the SRU are identified. The perimeters and areas of each of the second regions is recorded, as well as, the total count of the number of the identified irregular and varying second regions contained within the SRU.

Area Variability is the ratio of the area mean absolute deviation around the mean to the mean area expressed as a percentage and is calculated according to the following equation:

$$\text{Area Variability} = \frac{\frac{1}{n}\sum_{i=1}^{n}|x_i - \bar{x}|}{\bar{x}} \times 100$$

Where n is the number of individual second regions, $x_i$ are the individual second region areas, and) $\bar{x}$ is the arithmetic mean of all of the areas. The Area Variability is recorded to the nearest whole percent.

A shape complexity value is the ratio of a second region's perimeter squared to its area, and is calculated according to the following equation:

$$\text{shape complexity} = \frac{\text{perimeter}^2}{\text{area}}$$

Shape Variability is the ratio of the shape complexity mean absolute deviation around the mean to the mean shape complexity expressed as a percentage, and is calculated according to the following equation:

$$\text{Shape Variability} = \frac{\frac{1}{n}\sum_{i=1}^{n}|y_i - \bar{y}|}{\bar{y}} \times 100$$

Where n is the number of individual second regions, $y_i$ are the individual second region shape complexity values, and $\bar{y}$ is the arithmetic mean of all of the shape complexity values. The Shape Variability is recorded to the nearest whole percent.

The percent area of the second regions within a repeat unit is calculated by first measuring the total interior area of the SRU. The areas of all the individual second regions, or portions thereof, located within the SRU are identified, summed together, and then divided by the total area of the SRU. The percent area of the second regions is calculated according to the following equation:

$$\% \text{ Area of Second Regions} = \frac{\text{Sum of Individual Second Region Areas}}{\text{Area of } SRU} \times 100\%$$

The percent area of the second regions is recorded to the nearest whole percent.

The percent area of the first region within the repeat unit is calculated according to the following equation:

% Area of First Region=100%−% Area of Second Regions

Repeat this procedure on five separate and distinct repeat unit areas. Report each of the measurements as the arithmetic mean of the five replicates.

Micro-CT Intensive Property Measurement Method

The micro-CT intensive property measurement method measures the basis weight, thickness and volumetric density values within visually discernable regions of a substrate sample. It is based on analysis of a 3D x-ray sample image obtained on a micro-CT instrument (a suitable instrument is the Scanco µCT 50 available from Scanco Medical AG, Switzerland, or equivalent). The micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. A 3D image of the sample is generated by collecting several individual projection images of the sample as it is rotated, which are then reconstructed into a single 3D image. The instrument is interfaced with a computer running software to control the image acquisition and save the raw data. The 3D image is then analyzed using image analysis software (a suitable image analysis software is MATLAB available from The Mathworks, Inc., Natick, Mass., or equivalent) to measure the basis weight, thickness and volumetric density intensive properties of regions within the sample.

Sample Preparation:

To obtain a sample for measurement, lay a single layer of the dry substrate material out flat and die cut a circular piece with a diameter of 30 mm.

If the substrate material is a layer of an absorbent article, for example a topsheet, outer cover nonwoven web, acquisition layer, distribution layer, or another component layer; tape the absorbent article to a rigid flat surface in a planar configuration. Carefully separate the individual substrate layer from the absorbent article. A scalpel and/or cryogenic spray (such as Cyto-Freeze, Control Company, Houston Tex.) can be used to remove a substrate layer from additional underlying layers, if necessary, to avoid any longitudinal and lateral extension of the material. Once the substrate layer has been removed from the article proceed with die cutting the sample as described above.

If the substrate material is in the form of a wet wipe, open a new package of wet wipes and remove the entire stack from the package. Remove a single wipe from the middle of the stack, lay it out flat and allow it to dry completely prior to die cutting the sample for analysis.

A sample may be cut from any location containing the visually discernible zone to be analyzed. Within a zone, regions to be analyzed are ones associated with a three-dimensional feature defining a microzone. The microzone comprises a least two visually discernible regions. A zone, three-dimensional feature, or microzone may be visually discernable due to changes in texture, elevation, or thickness. Regions within different samples taken from the same substrate material may be analyzed and compared to each other. Care should be taken to avoid folds, wrinkles or tears when selecting a location for sampling.

Image Acquisition:

Set up and calibrate the micro-CT instrument according to the manufacturer's specifications. Place the sample into the appropriate holder, between two rings of low density material, which have an inner diameter of 25 mm. This will allow the central portion of the sample to lay horizontal and be scanned without having any other materials directly adjacent to its upper and lower surfaces. Measurements should be taken in this region. The 3D image field of view is approximately 35 mm on each side in the xy-plane with a resolution of approximately 5000 by 5000 pixels, and with a sufficient number of 7 micron thick slices collected to fully include the z-direction of the sample. The reconstructed 3D image resolution contains isotropic voxels of 7 microns. Images are acquired with the source at 45 kVp and 133 µA with no additional low energy filter. These current and voltage settings may be optimized to produce the maximum contrast in the projection data with sufficient x-ray penetration through the sample, but once optimized held constant for all substantially similar samples. A total of 1500 projections images are obtained with an integration time of 1000 ms and 3 averages. The projection images are reconstructed into the 3D image, and saved in 16-bit RAW format to preserve the full detector output signal for analysis.

Image Processing:

Load the 3D image into the image analysis software. Threshold the 3D image at a value which separates, and removes, the background signal due to air, but maintains the signal from the sample fibers within the substrate.

Three 2D intensive property images are generated from the threshold 3D image. The first is the Basis Weight Image, To generate this image, the value for each voxel in an xy-plane slice is summed with all of its corresponding voxel values in the other z-direction slices containing signal from the sample. This creates a 2D image where each pixel now has a value equal to the cumulative signal through the entire sample.

In order to convert the raw data values in the Basis Weight Image into real values a basis weight calibration curve is generated. Obtain a substrate that is of substantially similar composition as the sample being analyzed and has a uniform basis weight. Follow the procedures described above to obtain at least ten replicate samples of the calibration curve substrate. Accurately measure the basis weight, by taking the mass to the nearest 0.0001 g and dividing by the sample area and converting to grams per square meter (gsm), of each of the single layer calibration samples and calculate the average to the nearest 0.01 gsm. Following the procedures described above, acquire a micro-CT image of a single layer of the calibration sample substrate. Following the procedure described above process the micro-CT image, and generate a Basis Weight Image containing raw data values. The real basis weight value for this sample is the average basis weight value measured on the calibration samples. Next, stack two layers of the calibration substrate samples on top of each other, and acquire a micro-CT image of the two layers of calibration substrate. Generate a basis weight raw data image of both layers together, whose real basis weight value is equal to twice the average basis weight value measured on the calibration samples. Repeat this procedure of stacking single layers of the calibration substrate, acquiring a micro-CT image of all of the layers, generating a raw data basis weight image of all of the layers, the real basis weight value of which is equal to the number of layers times the average basis weight value measured on the calibration samples. A total of at least four different basis weight calibration images are obtained. The basis weight values of the calibration samples must include values above and below the basis weight values of the original sample being analyzed to ensure an accurate calibration. The calibration curve is generated by performing a linear regression on the raw data versus the real basis weight values for the four calibration samples. This linear regression must have an $R^2$ value of at least 0.95, if not repeat the entire calibration procedure. This calibration curve is now used to convert the raw data values into real basis weights.

The second intensive property 2D image is the Thickness Image. To generate this image the upper and lower surfaces of the sample are identified, and the distance between these surfaces is calculated giving the sample thickness. The upper surface of the sample is identified by starting at the upper-most z-direction slice and evaluating each slice going through the sample to locate the z-direction voxel for all pixel positions in the xy-plane where sample signal was first detected. The same procedure is followed for identifying the lower surface of the sample, except the z-direction voxels located are all the positions in the xy-plane where sample signal was last detected. Once the upper and lower surfaces have been identified they are smoothed with a 15×15 median filter to remove signal from stray fibers. The 2D Thickness Image is then generated by counting the number of voxels that exist between the upper and lower surfaces for each of the pixel positions in the xy-plane. This raw thickness value is then converted to actual distance, in microns, by multiplying the voxel count by the 7 µm slice thickness resolution.

The third intensive property 2D image is the Volumetric Density Image. To generate this image, divide each xy-plane pixel value in the Basis Weight Image, in units of gsm, by the corresponding pixel in the Thickness Image, in units of microns. The units of the Volumetric Density Image are grams per cubic centimeter (g/cc).

Micro-CT Basis Weight, Thickness and Volumetric Density Intensive Properties:

Begin by identifying the region to be analyzed. A region to be analyzed is one associated with a three-dimensional feature defining a microzone. The microzone comprises a least two visually discernible regions. A zone, three-dimensional feature, or microzone may be visually discernable due to changes in texture, elevation, or thickness, Next, identify the boundary of the region to be analyzed. The boundary of a region is identified by visual discernment of differences in intensive properties when compared to other regions within the sample. For example, a region boundary can be identified based by visually discerning a thickness difference when compared to another region in the sample. Any of the intensive properties can be used to discern region boundaries on either the physical sample itself of any of the micro-CT intensive property images. Once the boundary of the region has been identified, draw an oval or circular "region of interest" (ROI) within the interior of the region. The ROE should have an area of at least 0.1 mm2, and be selected to measure an area with intensive property values representative of the identified region. From each of the three intensive property images calculate the average basis weight, thickness and volumetric density within the ROI. Record these values as the region's basis weight to the nearest 0.01 gsm, thickness to the nearest 0.1 micron and volumetric density to the nearest 0.0001 g/cc.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this present disclosure.

What is claimed is:

1. A nonwoven web for an absorbent article, the nonwoven web comprising:
    a first surface;
    a second surface; and
    a plurality of repeat units, wherein each repeat unit has a same visually discernible pattern, the visually discernible pattern comprising a plurality of three-dimensional features comprising one or more first regions and a plurality of second regions, the one or more first regions have an average intensive property having a first value and the plurality of second regions have the average intensive property having a second, different value, wherein the average intensive property is basis weight, caliper, and/or volumetric density,
    wherein the one or more first regions comprise a plurality of substantially linear segments comprising a first group of irregularly spaced substantially linear segments intersecting with a second group of irregularly spaced substantially linear segments at angles of intersection,
    the irregularly spaced substantially linear segments of the first group extending in a first direction or within about 0.1 to about 10 degrees of the first direction, including one or more substantially linear segments comprising a portion that is slightly curved or non-straight with respect to the first direction such that the one or more substantially linear segments extend partially in a first direction and partially within about 0.1 to about 10 degrees of the first direction or partially at a first angle within about 0.1 to about 10 degrees of the first direction and partially at a second angle within about 0.1 to about 10 degrees of the first direction,
    the irregularly spaced substantially linear segments of the second group extending in a second direction or within about 0.1 to about 10 degrees of the second direction, including one or more substantially linear segments comprising a portion that is slightly curved or non-straight with respect to the second direction such that the one or more substantially linear segments extend partially in a second direction and partially within about 0.1 to about 10 degrees of the second direction or partially at a first angle within about 0.1 to about 10 degrees of the second direction and partially at a second angle within about 0.1 to about 10 degrees of the second direction,
    the first direction being traverse or substantially perpendicular to the second direction such that the angles of intersection are in the range of about 70 degrees to about 110 degrees, and
    wherein the plurality of second regions comprises 5 to 150 irregularly varying regions defined by the substantially linear segments substantially to fully enclosing or surrounding the irregularly varying regions having an area greater than 0.1 mm$^2$, according to the Pattern Analysis Test, the irregularly varying regions varying in shape and/or area.

2. The nonwoven web for an absorbent article of claim 1, wherein the angles of intersection are in the range of about 80 degrees to about 100 degrees.

3. The nonwoven web for an absorbent article of claim 1, wherein the one or more first regions have a % area of about 10% to about 30% and the plurality of second regions have a % area of about 70% to about 90% relative to an entire % area of the nonwoven web comprising the visually discernible pattern, according to the Pattern Analysis Test.

4. The nonwoven web for an absorbent article of claim 1, wherein the nonwoven web has a basis weight in the range of about 15 gsm to about 45 gsm, according to the Basis Weight Test.

5. The nonwoven web for an absorbent article of claim 1, wherein at least one substantially linear segment of the first group intersects three or more substantially linear segments of the second group.

6. The nonwoven web for an absorbent article of claim 1, wherein the first group and the second group of the plurality of substantially linear segments each comprise substantially linear segments of different lengths.

7. The nonwoven web for an absorbent article of claim 1, wherein the first group of linear segments includes multiple substantially linear segments having one or both endpoints terminating within the repeat unit such that the one or both endpoints do not terminate within or directly adjacent to and contacting first regions of the second group, and the second group of linear segments includes multiple substantially linear segments having one or both endpoints terminating within the repeat unit such that the one or both endpoints do not terminate within or directly adjacent to and contacting first regions of the first group.

8. An absorbent article comprising the nonwoven web of claim 1.

9. The absorbent article of claim 8, comprising:
a liquid permeable topsheet;
a liquid impermeable backsheet;
an absorbent core positioned intermediate the topsheet and the backsheet; and
an outer cover fibrous material forming a garment-facing surface of the absorbent article.

10. The absorbent article of claim 9, wherein the outer cover fibrous material and/or the liquid permeable topsheet comprises the nonwoven web.

11. A nonwoven web for an absorbent article, the nonwoven web comprising:
a first surface;
a second surface; and
a plurality of repeat units, wherein each repeat unit has a same visually discernible pattern, the visually discernible pattern comprising a plurality of three-dimensional features comprising one or more first regions and a plurality of second regions, the one or more first regions have an average intensive property having a first value and the plurality of second regions have the average intensive property having a second, different value, wherein the average intensive property is basis weight, caliper, and/or volumetric density,
wherein the one or more first regions comprise a plurality of substantially linear segments comprising a first group of irregularly spaced substantially linear segments intersecting with a second group of irregularly spaced substantially linear segments at angles of intersection,
the irregularly spaced substantially linear segments of the first group extending in a first direction or within about 0.1 to about 10 degrees of the first direction, including multiple substantially linear segments having one or both endpoints terminating within the repeat unit such that the one or both endpoints do not terminate within or directly adjacent to and contacting first regions of the second group,
the irregularly spaced substantially linear segments of the second group extending in a second direction or within about 0.1 to about 10 degrees of the second direction, including multiple substantially linear segments comprising one or both endpoints terminating within the repeat unit such that one or both endpoints do not terminate within or directly adjacent to and contacting first regions of the first group,
the first direction being traverse or substantially perpendicular to the second direction such that the angles of intersection are in the range of about 70 degrees to about 110 degrees, and
wherein the plurality of second regions comprises 5 to 150 irregularly varying regions defined by the substantially linear segments substantially to fully enclosing or surrounding the irregularly varying regions having an area greater than 0.1 mm$^2$, according to the Pattern Analysis Test, the irregularly varying regions varying in shape and/or area.

12. The nonwoven web for an absorbent article of claim 1, wherein the angles of intersection are in the range of about 80 degrees to about 100 degrees.

13. The nonwoven web for an absorbent article of claim 1, wherein the one or more first regions have a % area of about 10% to about 30% and the plurality of second regions have a % area of about 70% to about 90% relative to an entire % area of the nonwoven web comprising the visually discernible pattern, according to the Pattern Analysis Test.

14. The nonwoven web for an absorbent article of claim 1, wherein the nonwoven web has a basis weight in the range of about 15 gsm to about 45 gsm, according to the Basis Weight Test.

15. The nonwoven web for an absorbent article of claim 1, wherein at least one substantially linear segment of the first group intersects three or more substantially linear segments of the second group.

16. The nonwoven web for an absorbent article of claim 1, wherein the first group and the second group of the plurality of substantially linear segments each comprise substantially linear segments of different lengths.

17. The nonwoven web for an absorbent article of claim 1, wherein the first group of linear segments includes one or more substantially linear segments comprising a portion that is slightly curved or non-straight with respect to the first direction such that the one or more substantially linear segments extend partially in a first direction and partially within about 0.1 to about 10 degrees of the first direction or partially at a first angle within about 0.1 to about 10 degrees of the first direction and partially at a second angle within about 0.1 to about 10 degrees of the first direction, and the second group of linear segments includes one or more substantially linear segments comprising a portion that is slightly curved or non-straight with respect to the second direction such that the one or more substantially linear segments extend partially in a second direction and partially within about 0.1 to about 10 degrees of the second direction or partially at a first angle within about 0.1 to about 10 degrees of the second direction and partially at a second angle within about 0.1 to about 10 degrees of the second direction.

18. An absorbent article comprising the nonwoven web of claim 1.

19. The absorbent article of claim 8, comprising:
a liquid permeable topsheet;
a liquid impermeable backsheet;
an absorbent core positioned intermediate the topsheet and the backsheet; and
an outer cover fibrous material forming a garment-facing surface of the absorbent article.

20. The absorbent article of claim 9, wherein the outer cover fibrous material and/or the liquid permeable topsheet comprises the nonwoven web.

* * * * *